(12) United States Patent
Hao et al.

(10) Patent No.: US 10,226,390 B2
(45) Date of Patent: Mar. 12, 2019

(54) ROLLED ABSORBENT PERSONAL CARE ARTICLES AND METHODS OF MAKING SAME

(71) Applicants: Xueen George Hao, Beijing (CN); Yun Ying Gan, Beijing (CN); Lin Miao, Beijing (CN); Chun Lei Pu, Beijing (CN); Kimberly-Clark Worldwide, Inc, Neenah, WI (US)

(72) Inventors: Xueen George Hao, Beijing (CN); Yun Ying Gan, Beijing (CN); Lin Miao, Beijing (CN); Chun Lei Pu, Beijing (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 337 days.

(21) Appl. No.: 15/107,158

(22) PCT Filed: Dec. 25, 2013

(86) PCT No.: PCT/CN2013/090394
§ 371 (c)(1),
(2) Date: Jun. 22, 2016

(87) PCT Pub. No.: WO2015/096049
PCT Pub. Date: Jul. 2, 2015

(65) Prior Publication Data
US 2016/0331604 A1 Nov. 17, 2016

(51) Int. Cl.
*A61F 13/551* (2006.01)
*A61F 13/15* (2006.01)
(Continued)

(52) U.S. Cl.
CPC .......... *A61F 13/5514* (2013.01); *A61F 13/15* (2013.01); *A61F 13/15747* (2013.01);
(Continued)

(58) Field of Classification Search
CPC .............. A61F 13/15747; A61F 13/474; A61F 13/5513; A61F 13/55135; A61F 13/5514; A61F 13/55145; A61F 13/5519
See application file for complete search history.

(56) References Cited

U.S. PATENT DOCUMENTS 4,597,759 A * 7/1986 Johnson ................ A61F 13/474
604/385.16
5,358,499 A 10/1994 Seidy
(Continued)

FOREIGN PATENT DOCUMENTS

CN 1794960 A 6/2006
CN 1823693 A 8/2006
(Continued)

*Primary Examiner* — Catharine L Anderson
(74) *Attorney, Agent, or Firm* — Kimberly-Clark Worldwide, Inc.

(57) ABSTRACT

A rolled absorbent personal care article includes a longitudinal direction, a transverse direction and a depth direction. The absorbent article component, absorbent article extension component, wrapper sheet component each have a longitudinal, transverse, and depth direction. Each of the absorbent article component and absorbent article extension component includes at least a topsheet layer and a backsheet layer, wherein the backsheet layer includes a garment-facing surface on which is situated a garment adhesive. The absorbent article component and the absorbent article extension component each include a peripheral edge, with the components being attached to the wrapper sheet component with the garment adhesive, such that the peripheral edges are adjacent one another. The absorbent article component and the absorbent article extension component are in a rolled configuration within the wrapper sheet component and secured in the rolled configuration.

17 Claims, 17 Drawing Sheets

(51) Int. Cl.
*A61F 13/56* (2006.01)
*A61F 13/84* (2006.01)

(52) U.S. Cl.
CPC ........ *A61F 13/551* (2013.01); *A61F 13/5611* (2013.01); *A61F 13/84* (2013.01); *A61F 2013/8497* (2013.01)

(56) References Cited

U.S. PATENT DOCUMENTS

| | | | |
|---|---|---|---|
| 5,827,251 A | 10/1998 | Moder et al. | |
| 5,986,165 A | 11/1999 | Moder et al. | |
| 6,932,802 B2 | 8/2005 | Luizzi, Jr. et al. | |
| 7,083,603 B2* | 8/2006 | Bryant | A61F 13/15756 604/385.05 |
| 7,908,824 B2* | 3/2011 | Kuroda | A61F 13/5514 53/116 |
| 7,927,322 B2 | 4/2011 | Cohen et al. | |
| 7,942,265 B2 | 5/2011 | Luzzatto et al. | |
| 8,734,413 B2* | 5/2014 | Dennis | A61F 13/4702 604/385.02 |
| 2002/0013566 A1 | 1/2002 | Chappell et al. | |
| 2003/0120235 A1 | 6/2003 | Boulanger | |
| 2005/0015052 A1* | 1/2005 | Klippen | A61F 13/55115 604/150 |
| 2005/0131376 A1 | 6/2005 | Wheeler et al. | |
| 2006/0058764 A1 | 3/2006 | Bohlen et al. | |
| 2006/0058770 A1 | 3/2006 | Bohlen et al. | |
| 2006/0161125 A1 | 7/2006 | Bohlen et al. | |
| 2007/0179466 A1 | 8/2007 | Tremblay et al. | |
| 2011/0270209 A1 | 11/2011 | Rainho | |
| 2011/0270210 A1 | 11/2011 | Rainho | |

FOREIGN PATENT DOCUMENTS

| | | |
|---|---|---|
| CN | 200957136 Y | 10/2007 |
| CN | 102256579 A | 11/2011 |
| JP | 09-117473 A | 5/1997 |
| JP | 2013-244127 A | 12/2013 |

* cited by examiner

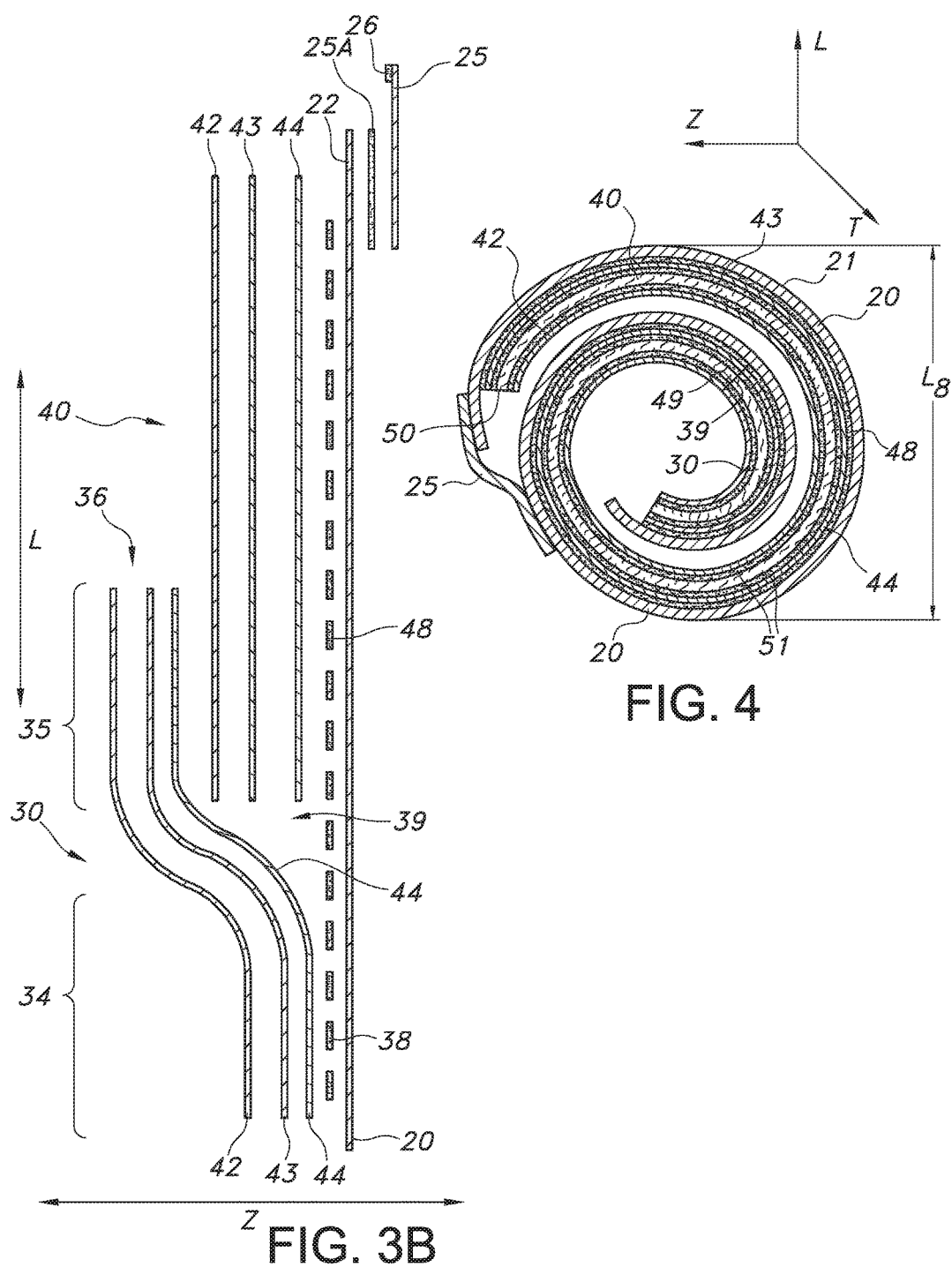

ROLLED ABSORBENT PERSONAL CARE ARTICLES AND METHODS OF MAKING SAME

RELATED APPLICATIONS

The present application is a national-phase entry, under 35 U.S.C. § 371, of PCT Patent Application No. PCT/CN2013/090394, filed on Dec. 25, 2013, which is incorporated herein by reference in a manner consistent with the instant application.

FIELD OF THE INVENTION

The present invention is generally directed to absorbent personal care articles. In particular, the present invention is directed to "rolled" format, feminine and adult hygiene absorbent personal care articles and their associated wrapper materials, and methods of producing such articles.

BACKGROUND OF THE INVENTION

Feminine and adult hygiene absorbent personal care articles are often used to protect consumer undergarments and outer garments from soiling, and to collect and retain body exudates containing menses, blood, or urine. Such articles are most commonly placed in the crotch region of garments during use. In the context of such products, comfort, absorbency, and discretion are three main product attributes and areas of concern for the wearers of such articles. In particular, wearers are often interested in knowing that such products will absorb body exudates in order to protect their undergarments, outer garments, or bedsheets from staining. Wearers are also interested in using products that cannot be seen or felt through their undergarments. Finally, wearers are interested in maintaining discretion with respect to the storage of such products prior to use, as well as during the removal of such products from their wrappers or packaging, in preparation for their use.

Feminine and adult hygiene absorbent personal care articles, such as sanitary napkins, pads and panty liners, and adult care undergarment inserts (as opposed to pant, brief, or diaper-type products), typically include at least one or more absorbent layers enclosed between a body-facing, liquid permeable topsheet layer and a garment-facing, liquid impermeable backsheet layer. The topsheet and backsheet layers are typically bonded or otherwise sealed together at their edges, forming a peripheral seal around the article, and sandwiching the absorbent layers there-between. Alternatively, a topsheet layer may be bonded or sealed to a backsheet layer, to offer lighter levels of protection, without the presence of a separate absorbent layer, per se, between them. In either event, such articles are frequently offered to consumers in individual wrappers or envelopes prior to use, in order to preserve their cleanliness until actual use. During use, such articles are often held in place to an undergarment via one or more pressure sensitive adhesive patches or strips, or alternatively, hook and loop style fasteners, positioned on the garment-facing surface of the backsheet layer. Some of these articles also include wing-like structures or extending foldable tabs, for wrapping about the edges of a user's undergarments to further secure them. Such wing-like structures are frequently integral with the absorbent article body, and are constructed from discrete, lateral extensions of both the topsheet and backsheet layers. Alternatively, the wing-like structures may be formed as separate attachments to the article.

The pressure sensitive adhesive patches or strips (also known as garment adhesive) on the garment-facing surface of the backsheet layer and wings (if present), are often covered by a removable, separate release sheet layer, or alternatively, by the article wrapper directly, so as to protect the pressure sensitive adhesive prior to use. Essentially, the separate release sheet layer or wrapper is in a face-to-face relationship with the garment adhesive. Such separate release sheet layer is frequently formed from a coated paper, nonwoven material, or film, and is either presented to the consumer by either being initially and temporarily attached to the article via the garment adhesive, or alternatively, by being more permanently attached to an article-facing surface of a wrapper, which is in turn, situated over the garment adhesive. A temporary connection is present between the garment adhesive and the release sheet. A separate release sheet layer is known to add costs and manufacturing challenges to such absorbent articles.

The release sheet layer or article-facing surface of the article wrapper as the case may be, is desirably coated on one or more surfaces with a peel-enhancing material, such as silicone, in order to facilitate removal/peeling of the article from the separate release sheet layer or wrapper during use. However, even with such coating, release sheets are known to produce an audible noise upon their removal from the article, or upon article removal from the wrapper, which noise can lead to embarrassment by the consumer at the time of readying the article for use.

The pressure sensitive adhesive patches, strips, or other fasteners are usually positioned in separated regions on the garment-facing surface of the article backsheet layer, generally along either the longitudinal or transverse directions of the article. Examples of such adhesive patches, strips, and release sheet/article wrapper combinations are described in U.S. Pat. No. 5,181,610 to Quick et al., U.S. Pat. No. 5,591,153 to Mattingly III, U.S. Pat. No. 6,500,160 to Mistune et al., U.S. Pat. No. 6,632,207 to Rangel et al., and United States Pat. Publication 2011/0009844 to Toro et al., each of which are hereby incorporated by reference thereto in their entirety.

The application of large patches of adhesive to the garment-facing surface of an article backsheet assists in maintaining the article in position within the undergarment, but often results in consumer difficulty in removal of the absorbent article from the release sheet or storage wrapper before use, and/or a consumer's undergarment after use. To this end, attempts have been made to provide tab-like structures on pads or in association with pads, to assist in their removal from wrappers before use, and undergarments after use. Such is described for example in U.S. Pat. No. 6,932,802 to Luizzi et al., and in European Patent 0699427 to Lefebvre Du Grosriez. However, such tab-like structures also add cost and manufacturing challenges to an article, and can lead to consumer confusion during article use.

There is therefore a need for an absorbent article and wrapper arrangement, which arrangement facilitates article removal from the wrapper without the need for a separate release sheet, with reduced audible noise, and without additional tab-like structures, on or in association with such article. There is a further need for such an article that adheres to an undergarment, but which can be easily removed at will by a consumer.

By the very nature of personal care absorbent articles, consumers often seek discretion both in article use, and also in article storage prior to use. Consumers often prefer that those persons around them not be aware that such articles are being worn, or being kept on a consumer's person (in unused form) prior to use. In this regard, absorbent personal care articles have been developed in "rolled" formats, such that they can be efficiently stored in discrete non-identifiable containers, or can be easily carried individually by consumers, in their pockets or purses, without being specifically recognized as being personal care absorbent articles. In such rolled configurations, the traditionally flat pads and liners are rolled about themselves, such that they take on a more tubular and compact configuration. For example, U.S. Pat. No. 5,827,251 to Moder et al., U.S. Pat. No. 7,041,091 to Wheeler et al., and United States Pat. Publication 2006/0161125 to Bohlen et al., each illustrate various rolled formats for storing liner and pad-style products prior to use. However, such products have presented unwrapping difficulties. Such products often retain their predisposition to curl once unrolled, making placement on an undergarment by a consumer challenging. Further, it is often difficult to initiate a peel of such articles from a previously rolled wrapper. Finally, the wrappers of such rolled products are often thin, posing manufacturing challenges. Therefore there is a need for such rolled products which can be easily manufactured and peeled during usage.

The large patches of garment adhesive preferred by consumers on backsheet layers, while helping to ultimately secure the pad or liner to a user's undergarment, can make unwrapping even more difficult in such "rolled" formats. There is therefore a need for a rolled absorbent article which can be easily removed from a wrapper, and which generally maintains its unrolled/flat shape prior to placement in an undergarment. Finally, there is a need for simplified manufacturing processes and product configurations which allow for "rolled" format, absorbent article production.

Depending on the specific daily needs of a consumer that uses absorbent personal care articles, such consumer may require extended length liners, pads, or inserts to accommodate the varying undergarment shapes, or varying fluid capture needs of a particular day. For example, it is known that at different times in a woman's monthly menstruation cycle, menstruation exudate amounts can vary. While numerous extended pad products have been developed to accommodate heavier exudate flows or larger surface areas of an undergarment, such as those described for example in U.S. Pat. No. 4,596,570 to Jackson et al. and U.S. Pat. No. 8,377,022 to Noda et al., there is still a need to efficiently produce extended pad products which are available in compact or "rolled" formats. There is a further need for such compact products in which the absorbent article and absorbent article extension are offered to a consumer in close physical proximity, for ease of use.

SUMMARY OF THE INVENTION

In accordance with a first embodiment of the invention, an absorbent personal care article includes a longitudinal direction, a transverse direction and a depth direction. The article includes an absorbent article component, an absorbent article extension component, and a wrapper sheet component each having a longitudinal, transverse, and depth direction. Each of the absorbent article component and the absorbent article extension component includes at least a topsheet layer and a backsheet layer, wherein the backsheet layer includes a garment-facing surface on which is situated a garment fastener. The absorbent article component and the absorbent article extension components each include a peripheral edge, the absorbent article component and the absorbent article extension component each being attached to the wrapper sheet component with the garment fastener, such that the peripheral edges are adjacent one another.

In an alternative embodiment of the invention, the absorbent article and the absorbent article extension components are in a rolled configuration within the wrapper sheet component and secured in the rolled configuration, such as by a tab tape, pressure sensitive adhesive, a roll encircling means or a combination thereof. In a further alternative embodiment, the adjacent peripheral edges are aligned. In yet a further alternative embodiment, the garment fastener is garment adhesive. In still a further alternative embodiment, the garment fastener is mechanical fastener, such as a hook and loop-type fastener. In another alternative embodiment, at least one of the absorbent article component and the absorbent article extension component include an absorbent core layer. In a further alternative embodiment, the garment fastener on the absorbent article component and the absorbent article extension component differs in strength between the absorbent article component and the absorbent article extension component, such that the absorbent article extension component has a greater propensity to stay with the wrapper sheet component than the absorbent article component does with the wrapper sheet component.

In another alternative embodiment, the absorbent article component and the absorbent article extension component are manufactured of the same types of layers. In still a further alternative embodiment, the absorbent article component and the absorbent article extension component are manufactured of the same types of materials. In yet another alternative embodiment, the peripheral edges are 30 mm or less from one another. In still another alternative embodiment, a peripheral edge of the absorbent article extension component overlaps a peripheral edge of the absorbent article component. In another alternative embodiment, the absorbent article component and the absorbent article extension component are aligned along either a longitudinal or transverse direction.

In yet another alternative embodiment, the absorbent article component and absorbent article extension component are visually distinguishable by peripheral edge shape differences, coloration differences, embossment differences, or a combination thereof. In still another alternative embodiment, the wrapper sheet component includes an article-facing surface, and further includes a release coating selectively positioned on the wrapper sheet component, article-facing surface. In another alternative embodiment, the wrapper sheet component includes different widths along its longitudinal direction. In a further alternative embodiment, the wrapper sheet component has a first end, a second end, and a middle region along the longitudinal direction between the first and second ends, and further wherein the first and second ends are wider along the transverse direction than the middle region. In still a further alternative embodiment, the wider first and second ends are sealed along the longitudinal direction at their lateral-most edges. In another alternative embodiment, the absorbent personal care article is selected from the group consisting of a panty liner, sanitary napkin, adult incontinence pad, garment insert and bed liner.

In still another alternative embodiment, a rolled absorbent personal care article includes a longitudinal direction, a transverse direction and a depth direction. The rolled absorbent personal care article includes an absorbent article component, an absorbent article extension component, and a wrapper sheet component each having a longitudinal, transverse, and depth direction. Each of the absorbent article component and the absorbent article extension component includes at least a topsheet layer and a backsheet layer, wherein the backsheet layer includes a garment-facing surface on which is situated a garment adhesive. The rolled absorbent article component and the absorbent article extension component each include a peripheral edge, with the absorbent article component and the absorbent article extension component each being attached to the wrapper sheet component with the garment adhesive, such that the peripheral edges are adjacent one another; and further, wherein the absorbent article component and the absorbent article extension components are in a rolled configuration within the wrapper sheet component and secured in the rolled configuration.

In an alternative, a method of manufacturing a rolled absorbent personal care article includes the steps of a) providing a unitary flat planar structure having a topsheet layer, a backsheet layer, and garment fastener on the backsheet layer, on a flat planar wrapper sheet component; b) separating or otherwise forming a separating seam in the unitary structure such that the unitary structure is separable into two components, the two components being an absorbent article component and an absorbent article extension component; c) rolling the wrapper sheet component about the absorbent article component and the absorbent article extension component to form a rolled absorbent personal care article; and d) securing the rolled absorbent personal care article in a rolled configuration.

In still a further alternative embodiment, a method of using the rolled absorbent personal care article includes the steps of a) unsecuring the rolled absorbent personal care article; b) unrolling the rolled absorbent personal care article to a relatively flat configuration; c) removing the absorbent article component from the wrapper sheet component, leaving the absorbent article extension component at least temporarily attached to the wrapper sheet component; and d) applying the absorbent article component to an undergarment. In still a further alternative embodiment of the method, the method further includes the steps of removing the absorbent article extension component from the wrapper sheet component; and applying the removed absorbent article extension component to the undergarment adjacent the absorbent article component. In still another alternative embodiment of the method, the method further includes the step of disposing of the wrapper sheet component and the attached absorbent article extension component as a unit.

Other features and aspects of the present invention are described in more detail below. Objects and advantages of the invention are set forth below in the following description, or may be learned through practice of the invention.

BRIEF DESCRIPTION OF THE DRAWINGS

A full and enabling disclosure of the present invention is set forth more particularly in the remainder of the specification, including reference to the accompanying figures, in which:

FIG. 3B illustrates an exploded cross-sectional view of an alternative embodiment of the unrolled panty liner, liner extension, and associated wrapper, with liner extension including an overlapping layer as also seen in FIG. 2E.

FIG. 4 illustrates a cross-sectional view of the panty liner, liner extension, and associated wrapper of FIG. 1 in rolled format, rolled along the longitudinal direction.

DEFINITIONS

Figure 1:
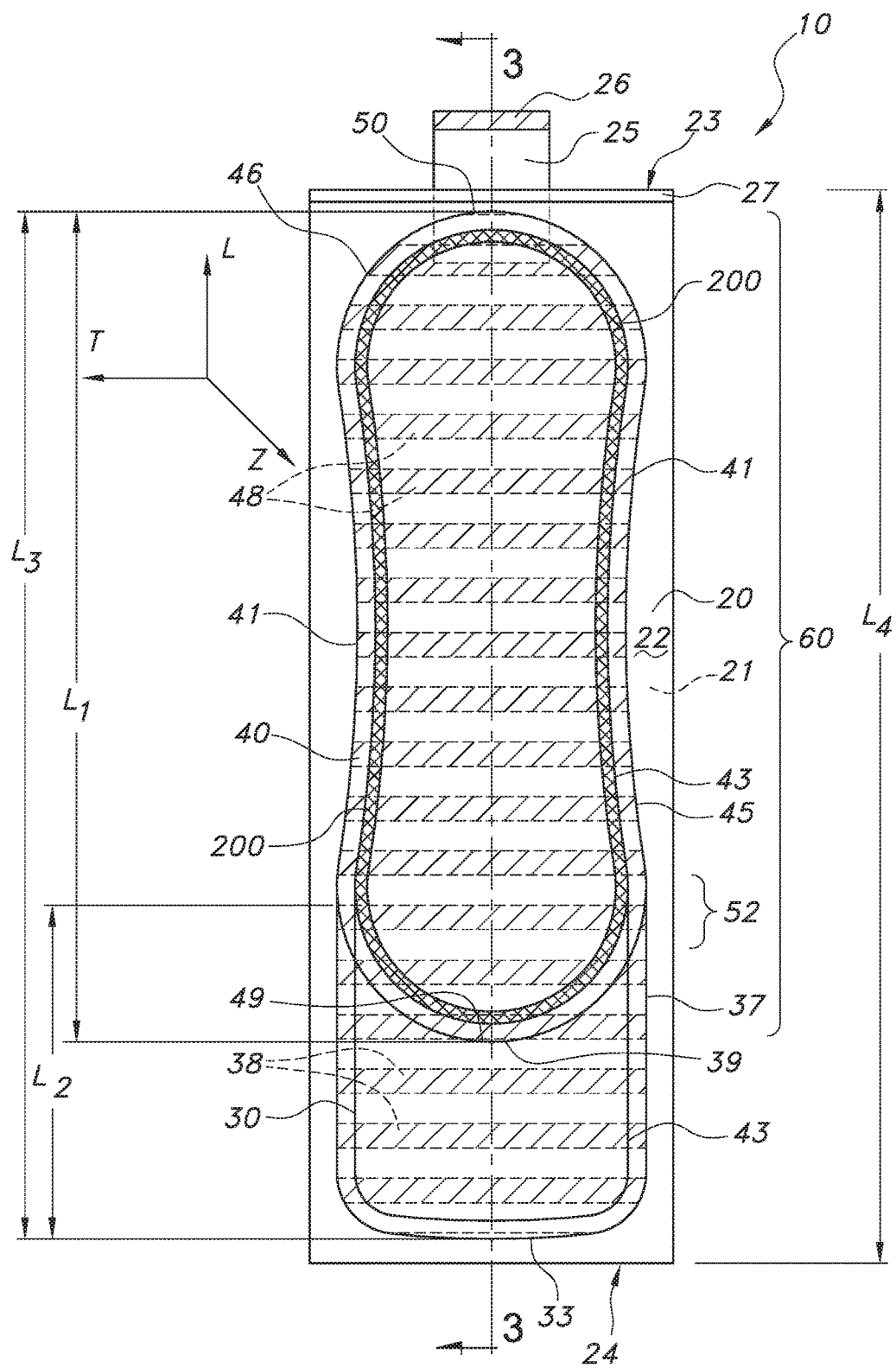
FIG. 1 illustrates a top plan view of an unrolled feminine care hygiene, absorbent personal care article in accordance with the invention, in the form of a panty liner and liner extension with associated wrapper.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, coform processes, and bonded carded web processes.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed fibers. Such a process is disclosed, for example, in U.S. Pat. No. 3,849,241 to Butin, et al., which is incorporated herein in its entirety by reference thereto. Generally speaking, meltblown fibers may be microfibers that are substantially continuous or discontinuous, generally smaller than 10 microns in diameter, and generally tacky when deposited onto a collecting surface.

As used herein, the term "spunbondweb" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto. Spunbond fibers are generally not tacky when they are deposited onto a collecting surface. Spunbond fibers may sometimes have diameters less than about 40 microns, such as between about 5 to about 20 microns.

As used herein, the term "coform" generally refers to composite materials comprising a mixture or stabilized matrix of thermoplastic fibers and a second non-thermoplastic material. As an example, coformed materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al. U.S. Pat. No. 5,284,703 to Everhart, et al. and U.S. Pat. No. 5,350,624 to Georger, et al. each of which are incorporated herein in their entirety by reference thereto.

For the purposes of this application, the term "rolled" shall refer to a planar sheet structure that is turned about itself, such as to overlap itself in a tubular configuration. To be rolled, a planar sheet structure is desirably formed in an initially flat configuration and then turned about itself from one end to another, desirably initially from an end not including a fastening means such as a tab tape, towards an end including a fastening means, such as a tab tape. It should be understood that other fastening means may be used instead of a tab tape, such as for example, self adherence through the use of a layer of pressure sensitive or other type of adhesive. In an alternative embodiment, the rolled article may be held in a secured configuration using a string, ribbon, or other encircling device. The turning (rolling) may occur about either the transverse or longitudinal directions of the planar sheet structure. Desirably in one embodiment, such rolled structure is not also folded with a distinct crease or fold line. Alternatively, one or more fold lines may be present in an embodiment. Such folds may be present along the article transverse or longitudinal directions. Desirably in one embodiment, the planar sheet structure is rolled about its transverse direction. In an alternative embodiment, the planar sheet structure is rolled about its longitudinal direction.

For the purposes of this application, the term "extension" shall refer to an additional planar sheet structure, aside from an absorbent article structure, but desirably in one embodiment of the same layered construction of an adjacent absorbent article structure. In a further alternative embodiment, such extension includes both the same types of layers (for example, functional layers) and also the same materials in the layers, as the layers of an adjacent absorbent article structure. For the purposes of this application, the term "adjacent" shall desirably refer to structures (such as separate structures) each having a peripheral edge or a portion thereof, that are located near or immediately next to one another (side-by-side) in the same horizontal plane of a layered structure. The term "adjacent" shall also refer to the proximate location of the peripheral edges of such structures. Such structures are illustrated for example in FIGS. 1, 2B, 2C, and 2D. For example, in one embodiment, such edges are at their closest distance, less than about 30 mm from one another, alternatively, between about 0 and 30 mm from one another, alternatively between about 0 and 5 mm from one another. Alternatively as noted, the term may refer to structures having peripheral edges that are near one another when viewed along the depth direction of the structure, but that are in separated planes. As with the previous distances, such distances of adjacent edges (but in separated planes) are in one embodiment less than 30 mm, alternatively, between about 0 and 30 mm, alternatively, between about 0 and 5 mm. Such spaced apart peripheral edges in different planes are illustrated for example in FIG. 3A. Such adjacent structures may alternatively in a further embodiment, overlap with one another such that a first portion of a first structure is in the same horizontal plane as a second structure, while a second portion of the first structure is in a different horizontal plane from the second structure when viewed through the depth direction of the overall structure. Such is illustrated for example, in FIGS. 2E and 3B. Desirably the peripheral edges of such structures are less than about 30 mm from one another, alternatively, between about 0 and 30 mm apart.

By incorporation of an absorbent article extension in addition to an absorbent article itself upon an associated wrapper sheet, it has been found that a rolled personal care absorbent article can be manufactured efficiently that allows both for ease of manufacture, ease of removal of the absorbent article from the wrapper, for general retention of an absorbent article's flat shape upon removal from the wrapper, and for the additional creation of a proximate absorbent-like structure in the form of an extension that may be optionally used by a consumer to extend an absorbent article length or width in use, if desired, and that can also be used as a wiping or cleaning surface.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures.

The rolled absorbent personal care articles of the present invention can be desirably used in feminine or adult hygiene, absorbent personal care product applications. For example, the rolled personal care absorbent article may take the form of a sanitary pad, panty liner, adult care absorbent garment insert, bed pad and the like. For ease of reference, absorbent feminine care panty liners are illustrated, but the invention is by no means limited to this product category type.

The absorbent personal care article component (having at least a topsheet, backsheet and one or more optional absorbent core layers) of the invention, is closely associated with an article wrapper sheet component, and is removable from the wrapper sheet component prior to use. The wrapper sheet component also includes in association therewith, additional topsheet and backsheet materials, and in some embodiments, additional absorbent core layer materials, these additional materials being in the form of at least one absorbent article extension component. Each of the additional materials of the at least one absorbent article extension component are desirably produced with the absorbent article layers (at the same time, but adjacent one another). Such at least one absorbent article extension component optionally remains with the wrapper sheet component, following removal of the absorbent article from the wrapper sheet component. Such additional extension materials may in one embodiment, be discarded along with the wrapper sheet as a unit, following removal of the absorbent article. Such additional topsheet, optional absorbent, and backsheet materials of the absorbent article extension component assist a consumer in the removal of the absorbent article from the associated wrapper sheet component, by providing a more rigid grasping point of separation, of the article from the associated wrapper sheet, and also may be used by a consumer at a later time, such as to provide for a removable pad or liner extension feature, if desired. The one or more absorbent article extension component(s) may be placed on the wrapper sheet component on the same side as the absorbent article component or on opposite sides. The one or more absorbent article extension component(s) may be placed adjacent either one side edge of the absorbent article component or adjacent multiple side edges of the absorbent article component, such as for example, adjacent either one or both end edges of the absorbent article component on the wrapper sheet component. It is contemplated that an absorbent article extension component may be adjacent both end edges, in the case of a single absorbent article and two absorbent article extensions combination. Such absorbent article and extension(s) components would essentially be in a side-by-side configuration on the wrapper sheet in one embodiment. The shapes of the absorbent article and absorbent article extension components may be such that their respective peripheral edges, or a portion thereof are aligned (nested, mated, or fitted) with one another. The peripheral edge of one component may be nested with the peripheral edge of the other component on the wrapper sheet component, or they may each be distinct from one another. For example, the absorbent article component may be of a generally dog-bone or oval shape, while the absorbent article extension component may include a mated peripheral edge shape, or a distinct oval, circular, or other non-mated geometric shape.

As can be specifically seen in FIG. 1, a top plan view of a generally planar personal care absorbent article structure, absorbent article extension structure, and associated wrapper sheet combination 10 is illustrated. The absorbent article component, absorbent article extension component, and associated wrapper sheet component, combination 10 are illustrated in their flat, unrolled form, for ease of viewing. The absorbent article component in the figure is specifically an absorbent panty liner.

The combination 10 includes a generally planar wrapper sheet component 20 in close association with a generally planar absorbent article component 40 (which in this case is the panty liner) and an absorbent article extension component 30. The absorbent article component 40, absorbent article extension component 30, and wrapper sheet 20 component (and combination 10) each have a longitudinal direction L (also known as machine direction or MD), a transverse direction T (also known as cross-machine direction or CD), and a depth direction Z. The wrapper sheet component 20 has an outwardly-facing surface 21, facing away from the absorbent article component 40 and in some embodiments the absorbent article extension component 30, and an inwardly directed article-facing surface 22. On the wrapper sheet component 20 of FIG. 1 are situated the absorbent article extension component 30 and the absorbent article component 40 (in this case the panty liner extension and panty liner). As shown, the absorbent article component 40 and absorbent article extension component 30 are shown with edges adjacent one another in the same horizontal plane (when viewed along the depth direction of the overall structure, as seen in the exploded cross-sectional view of FIG. 3). Such may alternatively be placed adjacent one another, but on opposite sides of the wrapper sheet component 20, as seen in FIG. 3A. In such an embodiment, the structures are in separated horizontal planes. The absorbent article extension component 30 and absorbent article component 40 are each shown in FIG. 1 in a side-by-side arrangement on the article facing surface 22 of the wrapper sheet component 20. The absorbent article extension component 30 and absorbent article component 40 are side-by-side one another along at least a portion of their adjacent peripheral edges, separated by a separation seam 39. The absorbent article component 40 has a linear distance or length L1 along the longitudinal direction (from an absorbent article component first end 49 to an absorbent article component second end 50). In one embodiment, the absorbent article component length L1 is between about 20 mm and 450 mm. In a second embodiment, the length L1 is between about 120 mm and 240 mm.

Figure 2:
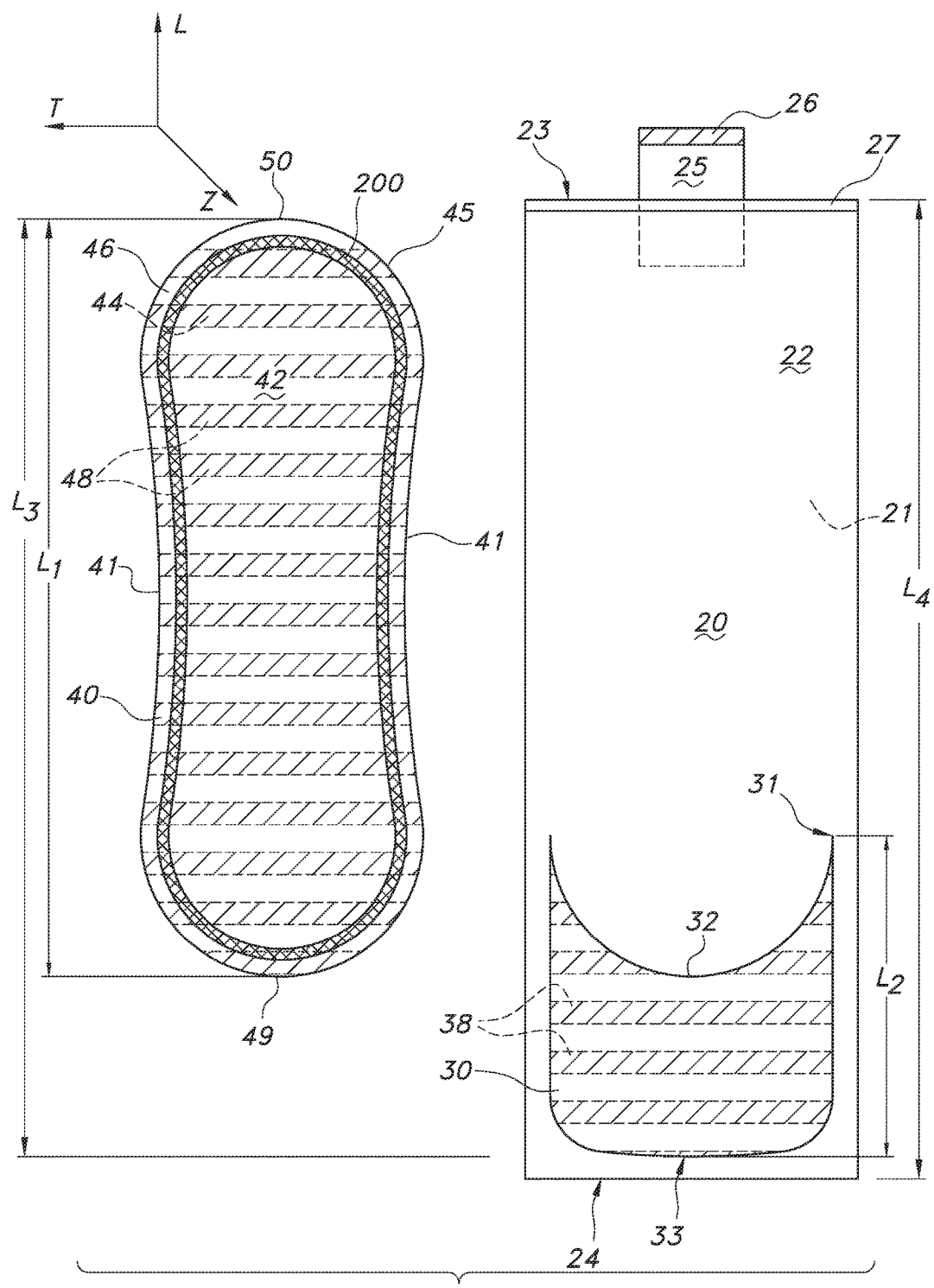
FIG. 2 illustrates a top plan view of the panty liner of FIG. 1 separated from the associated wrapper, with liner extension still attached to the wrapper.

The absorbent article extension component 30 has a linear distance or length L2 (from an absorbent article extension component first end 31 to an absorbent article extension component second end 33 (as seen in FIG. 2)). In one embodiment, the absorbent article extension component length L2 is between about 10 mm and 450 mm. In a second embodiment, the length L2 is between about 10 and 180 mm, alternatively between about 30 mm and 180 mm, alternatively between about 30 mm and 100 mm, alternatively between about 30 and 70 mm, alternatively about 50 mm. The combination of absorbent article component 40 and absorbent article extension component 30 have a total overall linear distance or length L3 from an absorbent article component end 50 to an absorbent article extension component end 33. In one embodiment such length L3 is between about 30 mm and 530 mm. In a further alternative embodiment it is desirable for the length of the absorbent article component 40 and absorbent article extension component to be in total L3, about 190 mm, with the absorbent article component 40 being about 150 mm, and the absorbent article extension component being about 40 mm. Still in a further alternative embodiment, the length L3 is between about 150 mm and 190 mm. In a further alternative embodiment, the ratio of L1 to L2 is between about 10 to 1 and about 4 to 1.

The associated wrapper sheet component 20 has a linear distance or length L4, from a wrapper sheet component first end 23 to a wrapper sheet component second end 24. In a first embodiment, the wrapper sheet component length L4 is between about 30 mm and 540 mm. In a second embodiment, the wrapper sheet component length L4 is between about 145 mm and 325 mm. Desirably in one embodiment, the wrapper sheet component length is longer than the combined length of the absorbent article component and absorbent article extension component. In an alternative embodiment, the wrapper sheet component length is less than the combined length of the absorbent article component and absorbent article extension component. For instance, desirably in one embodiment, the ratio of the length of the wrapper sheet component 20 (L4) to the overall length of the absorbent article component and absorbent article extension component (L3 on FIG. 1) is between about 0.8 to 1.5, alternatively, between about 1 to 1.2.

Figures 2A, 2B:
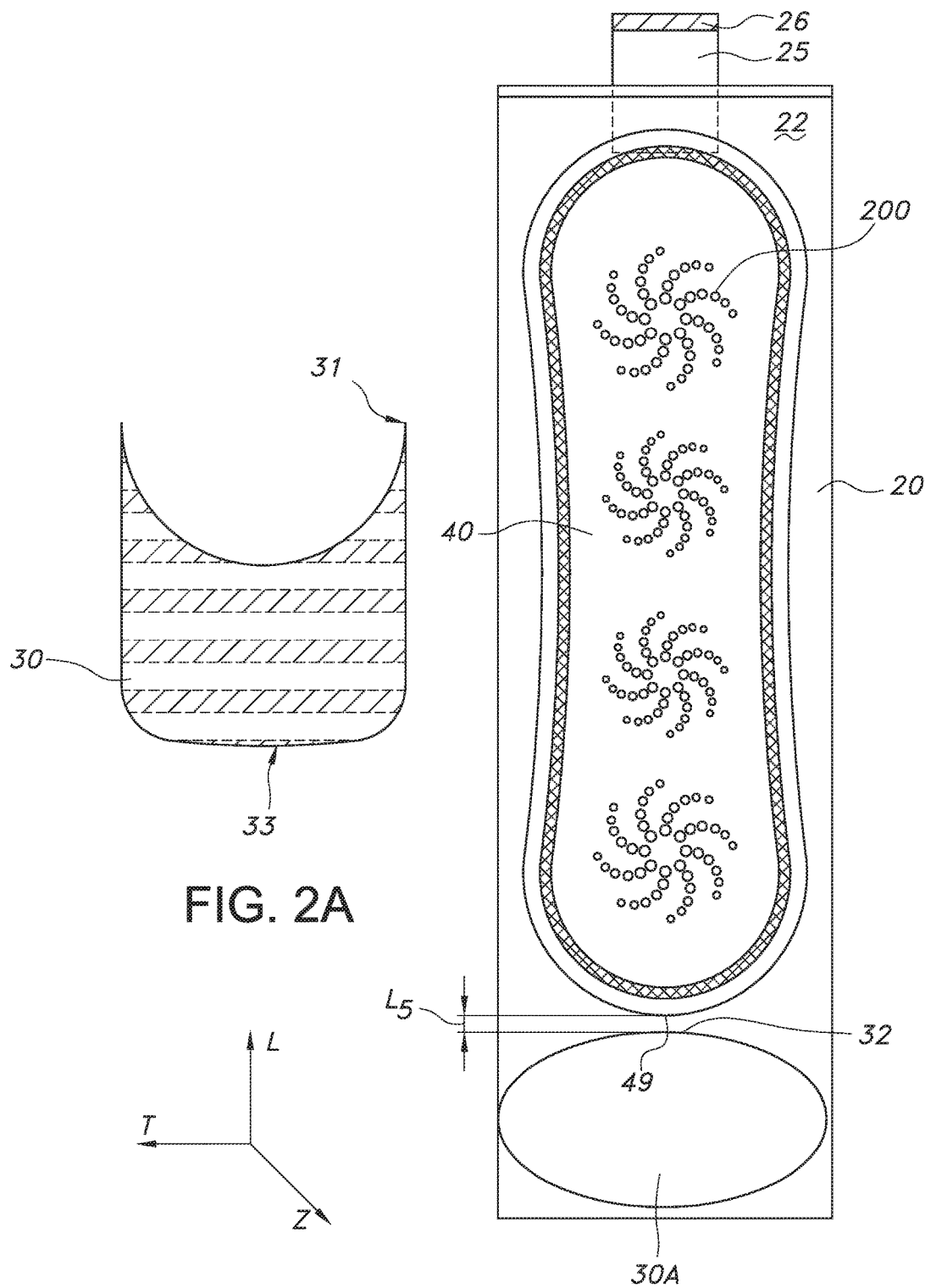
FIG. 2A illustrates a top plan view of the panty liner extension of FIG. 1 separated from the associated wrapper.
FIG. 2B illustrates a top plan view of an alternative embodiment of the unrolled panty liner of FIG. 1, with liner extension and associated wrapper.
Figure 2C:
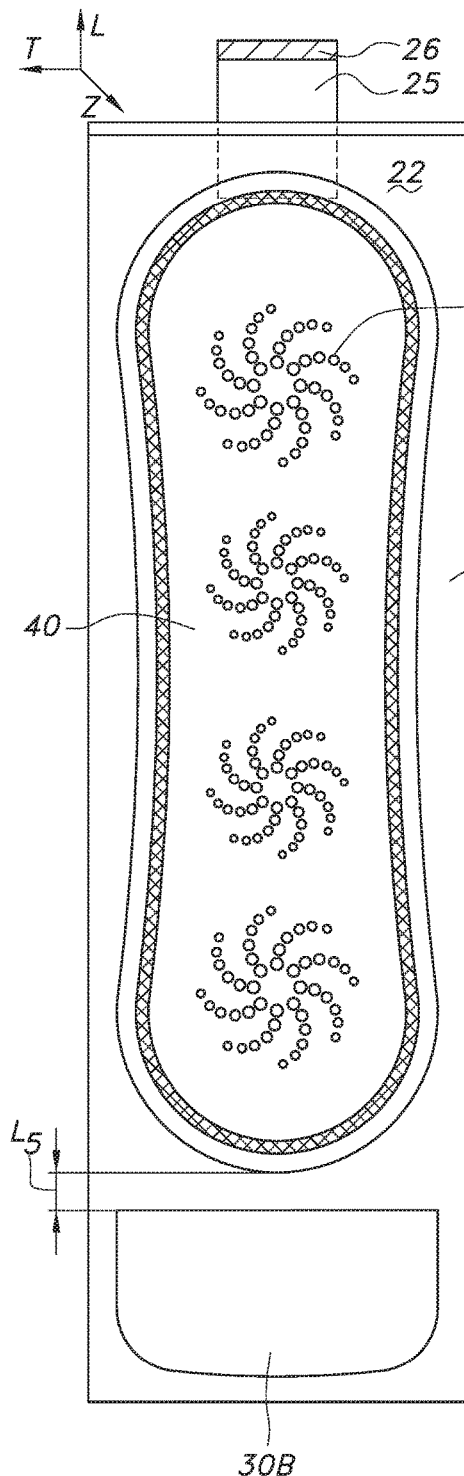
FIG. 2C illustrates a top plan view of an alternative embodiment of the unrolled panty liner of FIG. 1, with liner extension and associated wrapper.
Figure 2D:
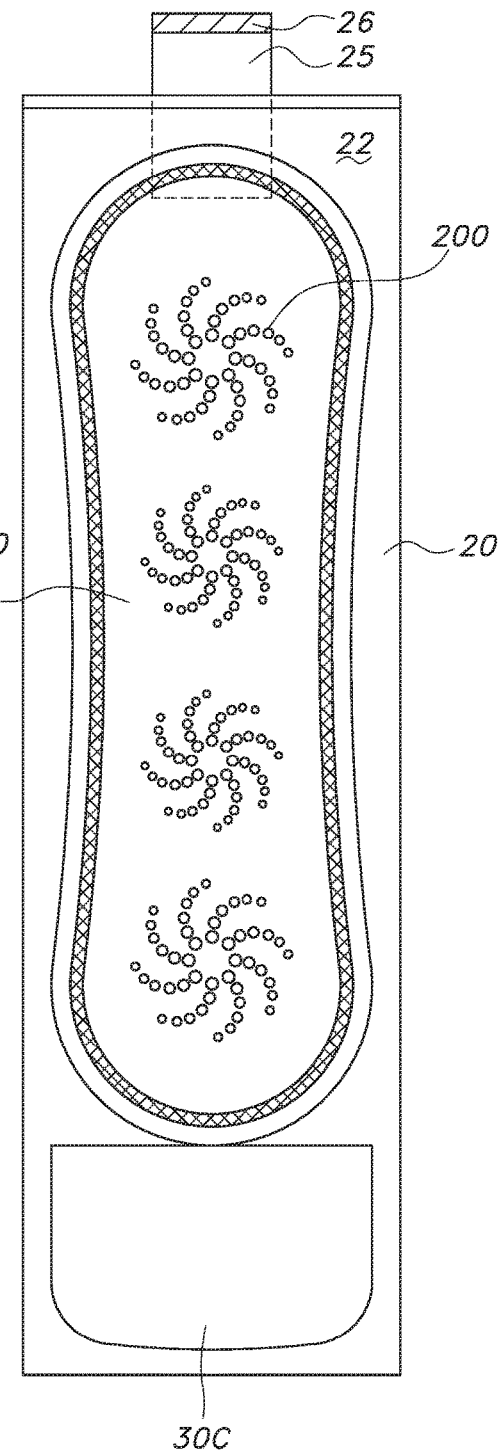
FIG. 2D illustrates a top plan view of still a further alternative embodiment of the unrolled panty liner of FIG. 1, with liner extension and associated wrapper.
Figure 2E:
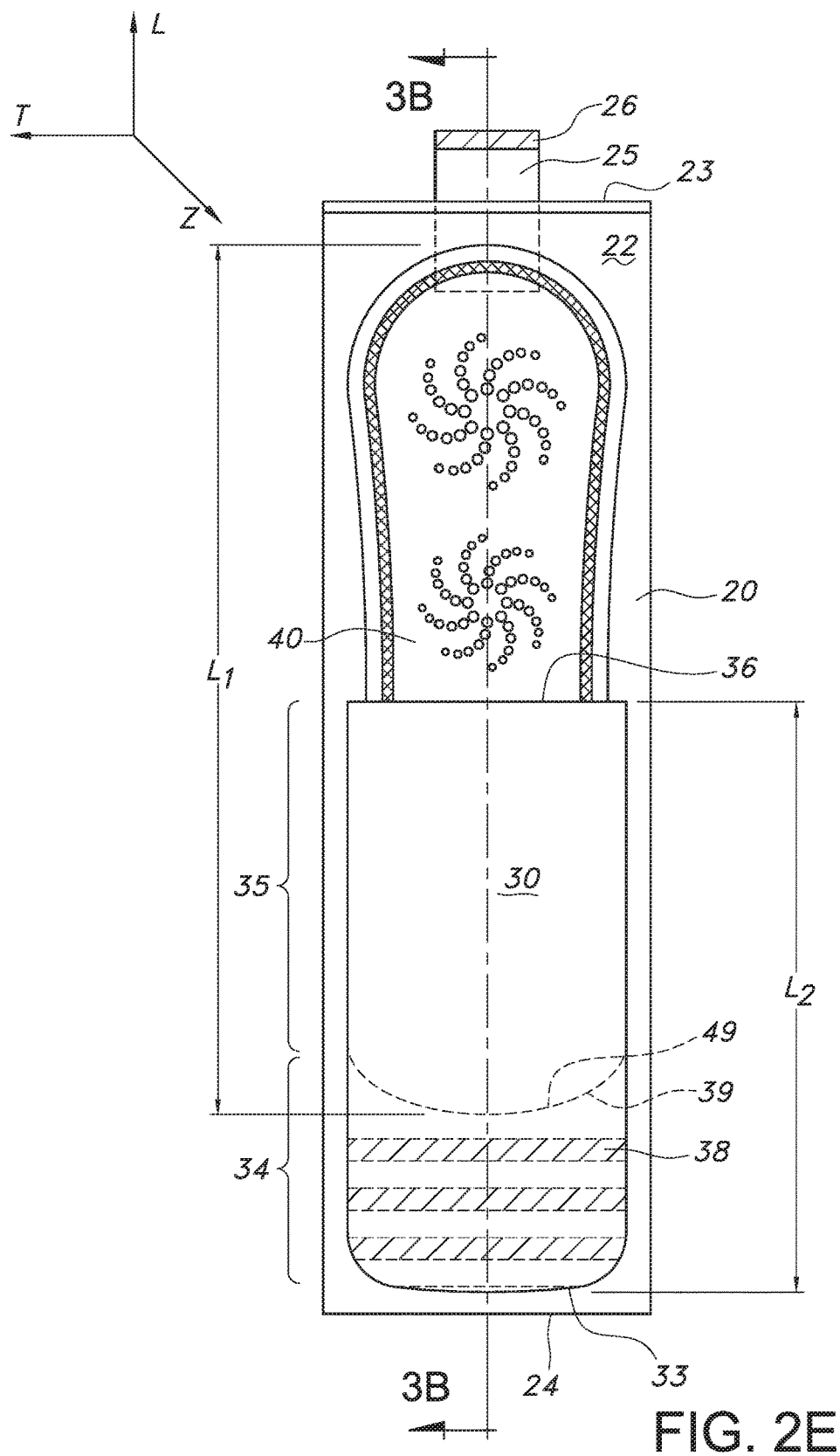
FIG. 2E illustrates a top plan view of another alternative embodiment of the unrolled panty liner of FIG. 1 with liner extension and associated wrapper, in which the liner extension includes an overlapping layer or portion.

In some embodiments, a visible spatial gap or separation space length L5 along the longitudinal direction (as seen in FIGS. 2B and 2C, separates the adjacent peripheral end edges of the absorbent article extension component from the absorbent article component. The gap or space length L5 between adjacent ends/edges may be along the same horizontal plane (as seen in FIG. 2B) or in different planes (as may occur for example in the embodiment of FIG. 3A). This linear distance or length L5 is desirably minimal. In a first embodiment, the linear distance L5 between the end peripheral edge 32 of the absorbent article extension component 30 and the end peripheral edge 49 of the absorbent article component 40 is about 0 mm, as they are immediately adjacent one another in the horizontal plane as seen in FIG. 1. In another embodiment, the separation distance L5 (as seen for example in FIGS. 2B-2D) between adjacent edges is less than about 30 mm, alternatively between about 0 and 30 mm, alternatively between about 0 and 5 mm. In a further alternative embodiment, the gap L5 is minimal when viewed in the depth direction, but the edges are physically separated along their length on opposite sides of the wrapper sheet component 20, when viewed in the depth direction as seen in FIG. 3A. The edges 49 and 32 are not aligned above and below the wrapper sheet component 20. In still a further alternative embodiment, the absorbent article extension component 30 overlaps the absorbent article component 40 when viewed from the depth direction, as seen in FIG. 2E and the cross-sectional view of FIG. 3B. While in this further alternative embodiment such edges (36, 49) are still desirably adjacent, they are in different horizontal planes. The overlapping portion 35 can be as much as 30 mm in length in one embodiment.

Figure 3:
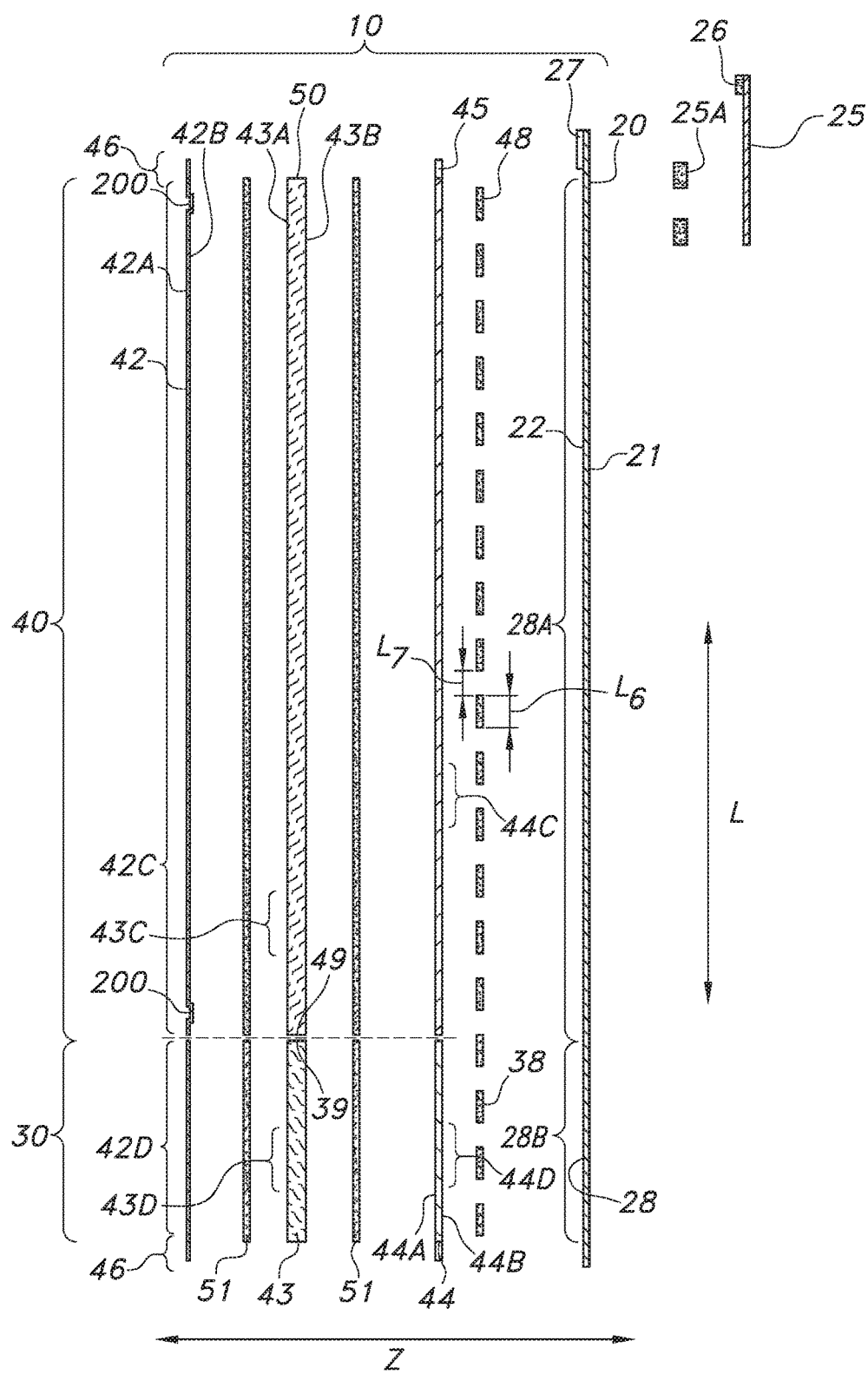
FIG. 3 illustrates an exploded cross-sectional view of the unrolled panty liner, liner extension, and associated wrapper of FIG. 1, taken along the longitudinal direction at line 3-3.
Figure 3A:
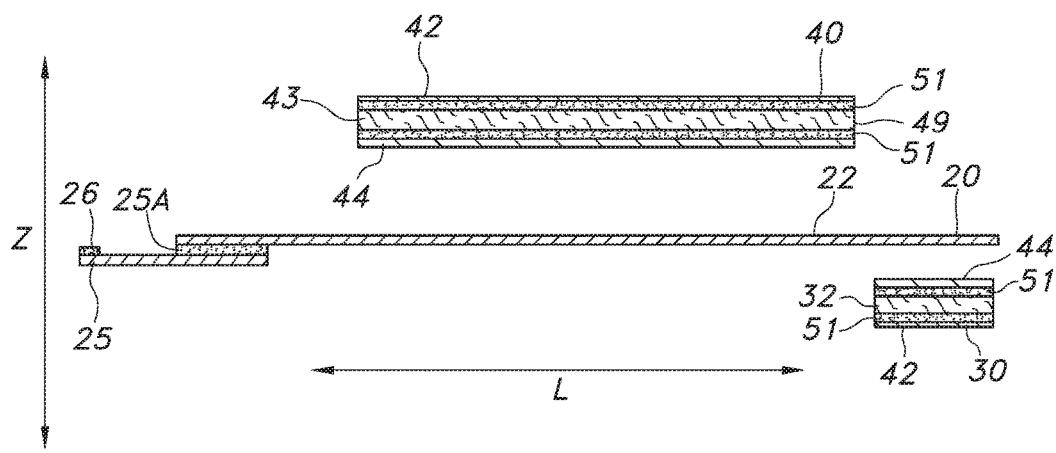
FIG. 3A illustrates an exploded cross-sectional view taken along the longitudinal direction, of an alternative embodiment of the unrolled panty liner, liner extension, and associated wrapper of FIG. 1, with liner extension on opposite side of the wrapper from the panty liner.
Figure 6:
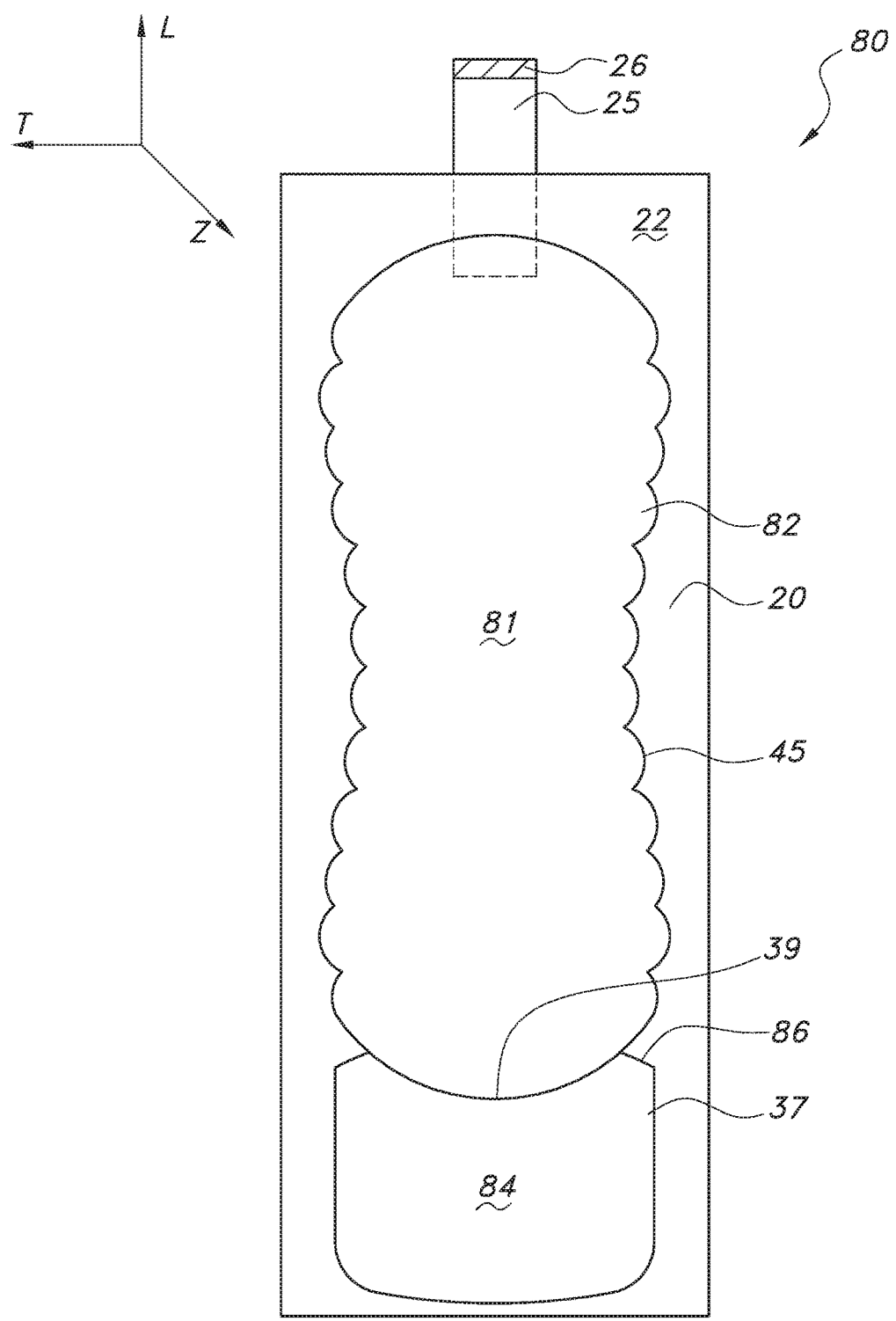
FIG. 6 illustrates a top plan view of a further alternate embodiment of the unrolled panty liner, liner extension, and associated wrapper of FIG. 1, with alternative peripheral edge shapes.

In the embodiment illustrated in FIGS. 1, 2, and 3, the absorbent article component and absorbent article extension component include the same number of layers and material structure for each of the layers. The respective outer peripheral edges (37, 45) of the absorbent article extension component 30 and absorbent article component 40 are desirably aligned 52 at select areas in which they are immediately adjacent, as with adjacent pieces of a jigsaw-style puzzle. By "aligned" is meant to describe a nesting or fitting of at least portions of component adjacent peripheral edges. A space or gap may separate the peripheral edges of the two components along the longitudinal direction. In a further embodiment of "aligned", the outer peripheral edge of one component 37 or an edge portion leads directly to or proximate to the outer peripheral edge 45 of the other component, such that there is little or no indentation or gap between them in this region (such as no gap or indentation between the mat the longitudinal edges along the longitudinal direction). Essentially, in one embodiment, the outer peripheral edge of one component leads to the outer peripheral edge of the other component, as a line would be tangential to a circle edge. This is in contrast to the gap or indentation illustrated in the alternative embodiment shown in FIG. 6 for instance, at feature 86. In FIG. 6, the outer peripheral edge 37 (longitudinally directed side edge) of the absorbent article extension component 84, while eventually leading to the outer peripheral edge 45 of the absorbent article component 81, creates a V-shaped indentation between them 86, such that the outer peripheral edge 37 is approximately perpendicular to, or at a relatively large angle with respect to the outer peripheral edge 45 of the absorbent article component 81 in at least one location. As shown in the Figure, the adjacent edges are still at least partially aligned/nested in certain portions, with minimal separation distance at the area of alignment along the separating seam 39. As will be further described with respect to other alternative embodiments, the adjacent peripheral edges need not be aligned, for example as in FIGS. 2B-2D. The absorbent article extension component 30 and absorbent article component 40 are in one embodiment (as seen in FIGS. 1, 2, and 3), made from the same planar sheet materials and during the same manufacturing processes, as will be described. Essentially, in such an embodiment, if the absorbent article component 40 is made from a topsheet layer, an absorbent layer and a backsheet layer, the absorbent article extension component 30 is likewise made from the same three layer types (and actual material types). If the absorbent article component 40 is made from only two layers bonded together (such as a topsheet layer and backsheet layer), the absorbent article extension component 30 is similarly made from the same two layers and material types. Therefore, in one embodiment, both the absorbent article extension component 30 and the absorbent article component 40 are absorbent (as including absorbent layers). In such an embodiment, the layers of the respective components are desirably made as a unitary structure and then a seam is created in order to separate the unitary structure into the two components 30, 40. The seam may be created either before or after the unitary structure is placed on the associated wrapper sheet component, desirably with care taken not to perforate or otherwise rip the associated wrapper sheet component. In another alternative embodiment, the absorbent article component 40 includes different layers than those of the absorbent article extension component 30. In such an embodiment, both components may be made in separate manufacturing processes and brought together such that the edges are adjacent, on the associated wrapper sheet component 20. For example, the absorbent article component 40 can include a topsheet layer, absorbent core layer, and a backsheet layer, while the absorbent article extension component 30 can include just a topsheet layer and a backsheet layer.

In FIGS. 1, 2, and 3, the absorbent article component 40 is shown as having an embossing pattern 200, such as in the shape of a race-rack design, adjacent the peripheral outer edge 45. Such an embossing pattern 200 is optional and may include any number of designs or patterns as are known in the art. For example, such pattern may be continuous or non-continuous, may be adjacent the peripheral edge 45 as shown, or alternatively may extend across a component of, or the entire surface of the absorbent article component 40 in the transverse direction (or a combination of transverse and longitudinal directions). Alternative swirl-style embossing patterns 200 are shown in FIGS. 2B-2F. Optionally, the absorbent article extension component 30 may also be embossed (not shown). In a further alternative embodiment (not shown), the embossment patterns of the absorbent article component and absorbent article extension component may be coordinated aesthetically, such that they include similarly shaped designs or spatially aligned designs. In yet a further alternative embodiment, the embossment patterns of the absorbent article component and absorbent article extension component may differ, such that the visual distinction between the two components is obvious to a consumer, making grasping points easier to identify for component separation. The embossment feature(s) 200 may penetrate into one or more layers of each of the components. Embossing techniques, such as those created by heat and pressure, are known in the art and therefore are not further described herein.

While not illustrated in the Figures, it should also be recognized that each of the absorbent article component and absorbent article extension component may be similarly printed (such as on the garment-facing side of their topsheet layer or the user-facing surface of their backsheet layer), or printed with different designs. As with differing embossing patterns between components, such printing differentiation may assist the consumer in identifying the location to grasp and separate the components from the wrapper sheet.

The absorbent article component 40 includes two longitudinally extending side edges 41, and two end edges 49, 50 as noted. As shown in FIGS. 1, 2, and 3, the absorbent article end edge 49 is desirably fitted/aligned with at least one end edge 32 (a portion of the peripheral edge) of the absorbent article extension component 30. The end edges (or portions thereof) of the absorbent article and absorbent article extension components may be either generally bordering in the same horizontal plane, as shown in FIGS. 1, 2D, 2F, 5, 6,7,8,9, and 10, separated from one another in the same horizontal plane as shown in FIGS. 2B, 2C, separated from one another in different horizontal planes as shown in FIG. 3A, or even partially overlapping, as shown in FIG. 2E.

As can be seen particularly in FIG. 3, which illustrates a cross-sectional view of the combination 10 of FIG. 1 taken along line 3-3, the absorbent article extension component 30 and absorbent article component 40 each include a topsheet layer 42, which extends along the length direction of the combination 10. The topsheet layer 42 includes a user-facing surface 42A and garment-facing surface 42B. The topsheet layer 42 is shown as embossed 200 adjacent the periphery. As noted, while shown as being only in the topsheet layer, such embossing feature 200 may optionally penetrate into other layers along the structure depth direction Z. One or more additional interior layers, such as an absorbent core layer 43, fluid transfer layer and/or fluid distribution layer 51 may be present in the absorbent article component 40. A backsheet layer 44 is situated subjacent the absorbent core layer or other fluid management layers in the Z direction. In one embodiment, the topsheet layer 42 and other subjacent layers in the Z direction are made as a unitary structure and each physically separated into two respective adjacent planar layers (such as 42C, 42D for the topsheet layer, 43C and 43D for the absorbent layer, 44C and 44D for the backsheet layer) at separation seam 39, so that the absorbent article extension component 30 can be physically separated from the absorbent article component 40 in use. In a first embodiment, the separation seam 39 is created through the depth direction Z of the materials making up the absorbent article extension component 30 and the absorbent article component 40 by traditional seam-forming techniques. For example, the separation seam 39, may be created by laser cutting/perforation, physical cutting/perforation, or melting techniques on the various layers in the structure during the manufacturing process. Alternatively, the separation seam may be created by the separate placement, or separate manufacture and placement, of the absorbent article component and absorbent article extension component adjacent one another with a gap between them. The separation seam 39 allows for the separation of the components without any force, or without significant force. Desirably, the separation seam 39 does not penetrate the wrapper sheet component 20. In an alternative embodiment, the separation seam 39 may not be a complete and continuous separation through all material layers of the absorbent article component 40 and absorbent article extension component 30, but may be instead formed from a series of perforations or weakened areas, through a unitary-formed structure, sufficient to allow separation without extreme force, ripping, or tearing of the layers (except for the wrapper sheet 20). It is desirable for example, in one embodiment for the absorbent article component 40 to be easily peeled off of the wrapper sheet component 20 while leaving the absorbent article extension component 30 in place (and adhesively attached) on the wrapper sheet component. Both the wrapper sheet component 20 and absorbent article extension component 30 may then be discarded if desired, in a single step.

As previously illustrated, the actual spatial separation of the absorbent article component 40 from the absorbent article extension component 30 on the wrapper sheet component may be by a relatively larger gap (as seen in FIGS. 2B and 2C) rather than a narrow almost indiscernible line. In such instances, the absorbent article extension component 30 can be manufactured separately and applied in separate steps to the wrapper sheet component 20. In such instances, the adjacent edges can also be of different, non-aligned configurations as shown. Different, non-aligned peripheral edge configurations may further distinguish the two components visually for ease of use (separation), if desired.

Figure 5:
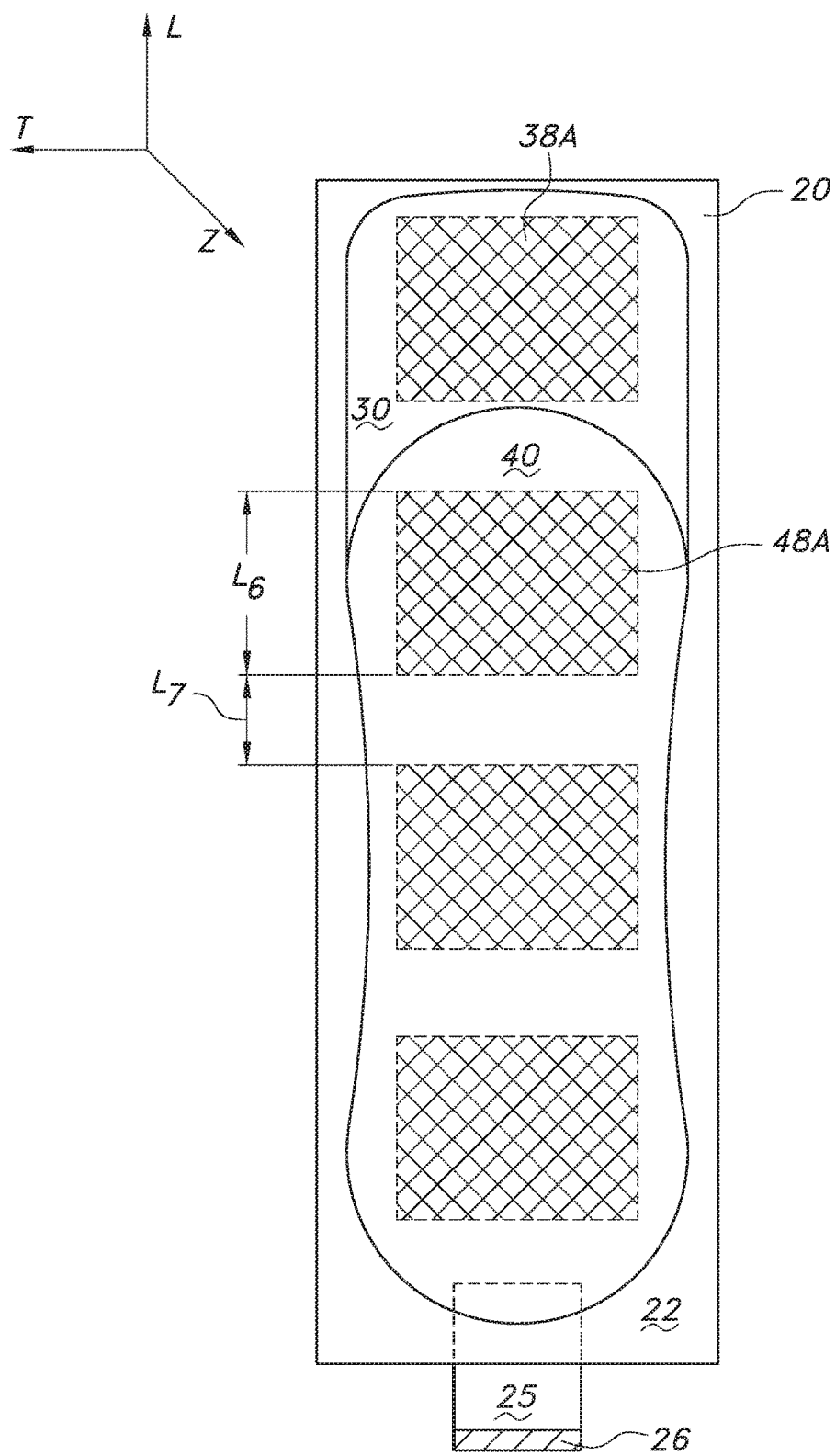
FIG. 5 illustrates a top plan view of an alternate embodiment of the unrolled panty liner, liner extension, and associated wrapper of FIG. 1, with alternative garment adhesive pattern shown in phantom.

As seen in FIG. 3, the backsheet layer 44 has a user-facing surface 44A and a garment-facing surface 44B. The absorbent article extension component 30 and absorbent article component 40 each respectively include garment fasteners such as garment adhesive patches, in one embodiment, in the form of alternating strips of adhesive 38, 48 which are shown in phantom in FIG. 1. The garment adhesive may be continuous or discontinuous across the garment-facing surface 44B of the backsheet layer 44. Alternating strips of adhesive 38, 48 (alternating with backsheet layer strips of material not having adhesive thereon) are illustrated running across the absorbent article component 40 and absorbent article extension component 30 transverse direction in FIG. 1, for the full longitudinal direction of the absorbent article component and absorbent article extension component. The garment adhesive patches, which initially adhere the article and extension components to the associated wrapper sheet component, and eventually to any undergarment, may be of a multitude of configurations, such as geometric shapes along the transverse or longitudinal directions. An alternative embodiment of the combination 10 is shown in FIG. 5, in which the garment adhesive patches 38A and 48A are present in relatively large, rectangularly-shaped blocks. In another embodiment in which there is overlap of a portion of the absorbent article extension component 30 and absorbent article component 40 (as seen in FIGS. 2E, and 3B), such garment adhesive patches 38 are only present on a non-overlapping, portion 34 of the absorbent article extension component 30, but not the overlapping portion 35 of the absorbent article extension component 30. In such an embodiment, the absorbent article extension component 30 includes an adjacent free edge 36, that is not tacked down onto the absorbent article component 40, which can be easily lifted upwards prior to separation of the absorbent article component 40 from the wrapper sheet component 20. Such overlapping portion 35 of the absorbent article extension component 30 can provide for further extension of the effective absorbent article length (combined length L3) if desired, once the absorbent article and absorbent article extension components are placed in an undergarment for use. Essentially in such an embodiment, the absorbent article extension component length L2, would be much larger than previously described embodiments, that is, the relative ratio of lengths of the absorbent article component to absorbent article extension component in FIG. 2E would be relatively smaller, compared to previously described embodiments. Such absorbent article and absorbent article extension use will be later described.

As noted, the garment adhesive patches can run in any number of directions along the garment-facing surface 44B of the backsheet layer. The garment adhesive patches have a length L6 along the longitudinal direction and a separation length (or distance) L7 between patches along the longitudinal direction. In a first embodiment, the length L6 is between about 1 mm and 530 mm, alternatively, between about 1 mm and 150 mm, alternatively, between about 2 mm and 5 mm. In another alternative embodiment, the separation length L7 is less than about 80 mm, alternatively between about 0 mm and 80 mm, alternatively between about 1 mm and 50 mm, alternatively, between about 2 mm and 10 mm.

Desirably, in one embodiment, garment adhesive covers between about 20 percent and 70 percent of the backsheet layer garment-facing surface area 44B, alternatively between about 30 and 50 percent of the backsheet layer garment-facing surface area. In a further alternative embodiment, the ratio of adhesive covered surface area between the absorbent article extension component (extension component backsheet, garment-facing surface area covered with adhesive) and the absorbent article component (absorbent article component backsheet, garment-facing surface area covered with adhesive) is between about 1:6 and 1:2. Alternatively, such garment adhesive strips may be in the illustrated block form, covering the same or a larger area of the backsheet garment-facing surface than the illustrated narrower strips (as seen in the adhesive blocks of FIG. 5), or alternatively in strips directed along the absorbent article longitudinal direction, rather than the transverse direction. It should be recognized that while the adhesive strips or blocks are shown as being uniform in shape and size, the shape and size of such adhesive patches may vary on a component or between components.

The garment adhesive strips 48, 48A, 38, 38A, 68 at least temporarily adhere to the wrapper sheet component 22 surface prior to article use. Such garment adhesive is desirably hot melt, pressure sensitive adhesive as is known in the adhesive art. Examples of such pressure sensitive adhesives are available from Henkel, Germany, and H. B. Fuller of the United States. Other examples of garment adhesive may be found in U.S. Pat. Publications 2005/256481 to Rosati et al. and 2005/203478 to Veglio et al., which are each incorporated by reference thereto in their entirety.

Figure 2F:
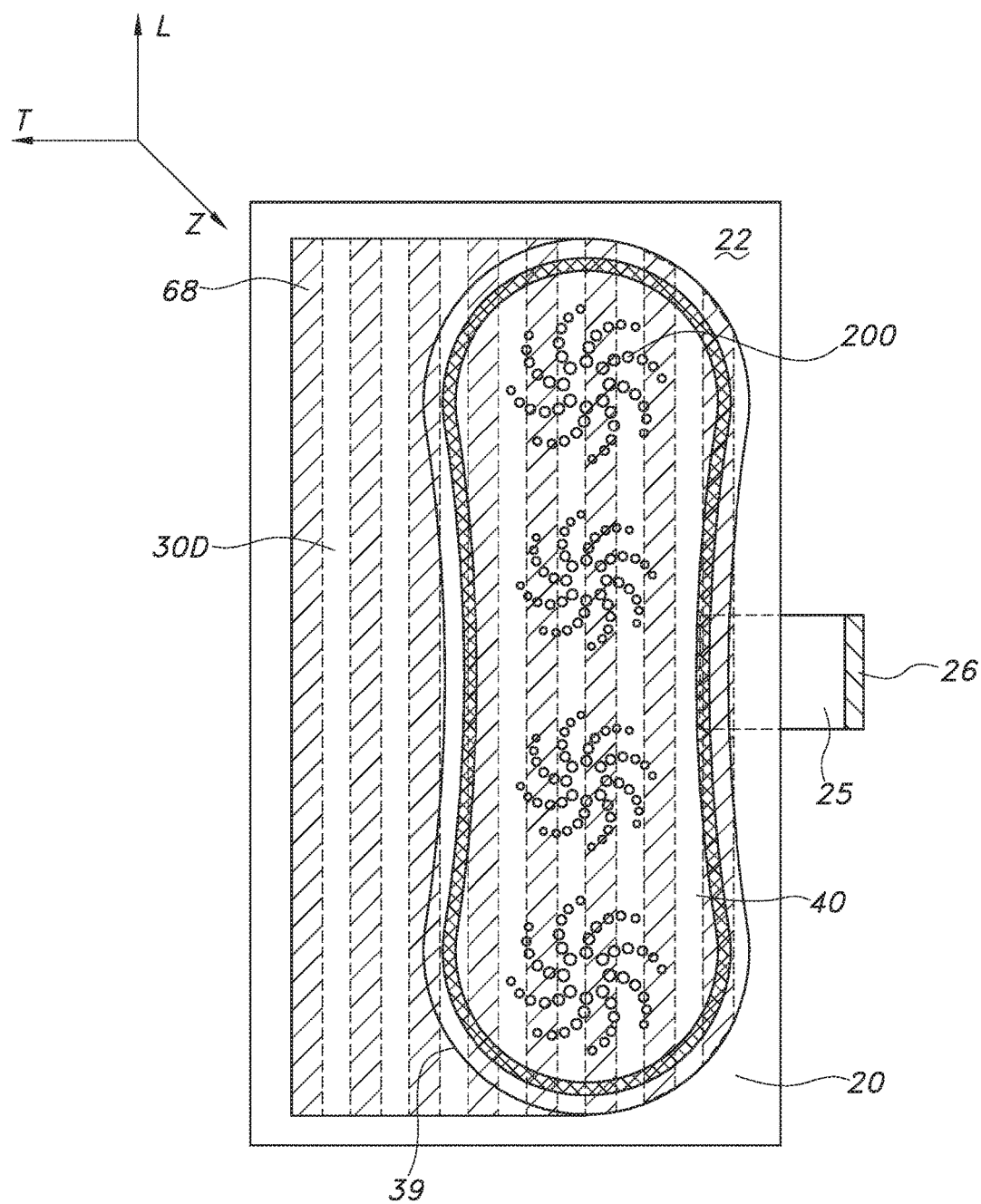
FIG. 2F illustrates a top plan view of yet a further alternative embodiment of the unrolled panty liner of FIG. 1, with liner extension and associated wrapper.

While shown in FIG. 1 as running along the transverse direction T, the adhesive patches may alternatively run in the longitudinal direction (as seen in FIG. 2F), or a combination of directions. Such adhesive patches may also run a width or length that does not continuously stretch from one edge or end of the absorbent article component or absorbent article extension component to the other, as seen in FIG. 5. In a further embodiment, by varying garment fastener (such as for example adhesive) strengths between the absorbent article component 40 and the absorbent article extension component 30, rolled articles can be produced which demonstrate a greater propensity for the absorbent article extension component 30 to remain with the wrapper sheet component than the absorbent article component 40. For instance, garment adhesive in one area, such as along the absorbent article extension component, can be more or less aggressive than in another area of the article. As an example, the ability to peel (the peelability or peel strength) the absorbent article extension component may be desirably more difficult than the ability to peel the absorbent article component, such that the absorbent article extension component preferably stays with the wrapper sheet component (and separates more easily from the absorbent article component, upon absorbent article removal from the wrapper sheet component). Essentially, one of the components would have a peel strength differing from the other. The bonding of one of the components would be different than the other, such that more force would be required to separate one component from the wrapper than the other component. In an alternative embodiment, rather than provide different adhesive strengths between the garment adhesive (or other type of garment fastener) of the absorbent article component and the garment adhesive (or other type of garment fastener) of the absorbent article extension component, different release surfaces may be provided on the wrapper sheet component surface adjacent to the garment adhesive (or other garment fastener) regions on the absorbent article and absorbent article extension components. For example, a release surface treatment such as silicone may be provided only on the wrapper sheet component surface area directly facing the garment adhesive of the absorbent article component, but not on the wrapper sheet component surface area directly facing the garment adhesive of the absorbent article extension component. Further, as shown in FIG. 1, a peripheral seal 46 seals at least the topsheet layer 42 to the backsheet layer 44 via traditional sealing methods, such as for example adhesive, thermal, or ultrasonic bonding.

It should also be recognized, that while not shown in the figures, rather than using garment adhesive strips, patches, or blocks, other forms of garment fastening devices may alternatively be used to adhere the absorbent article component and absorbent article extension component to the wrapper sheet component. For example, garment fasteners may include hook and loop devices, or other mechanical fastening systems to connect the two components. For instance, hooks may be placed on the absorbent article and absorbent article extension components for adherence to a nonwoven sheet on the facing wrapper sheet component. In a further alternative embodiment, each of the absorbent article and absorbent article extension components may include different types of garment fasteners on each of their respective backsheets. The garment fasteners/devices provide at least temporary attachment of each of the absorbent article component and absorbent article extension component to the wrapper sheet component.

Figure 11:
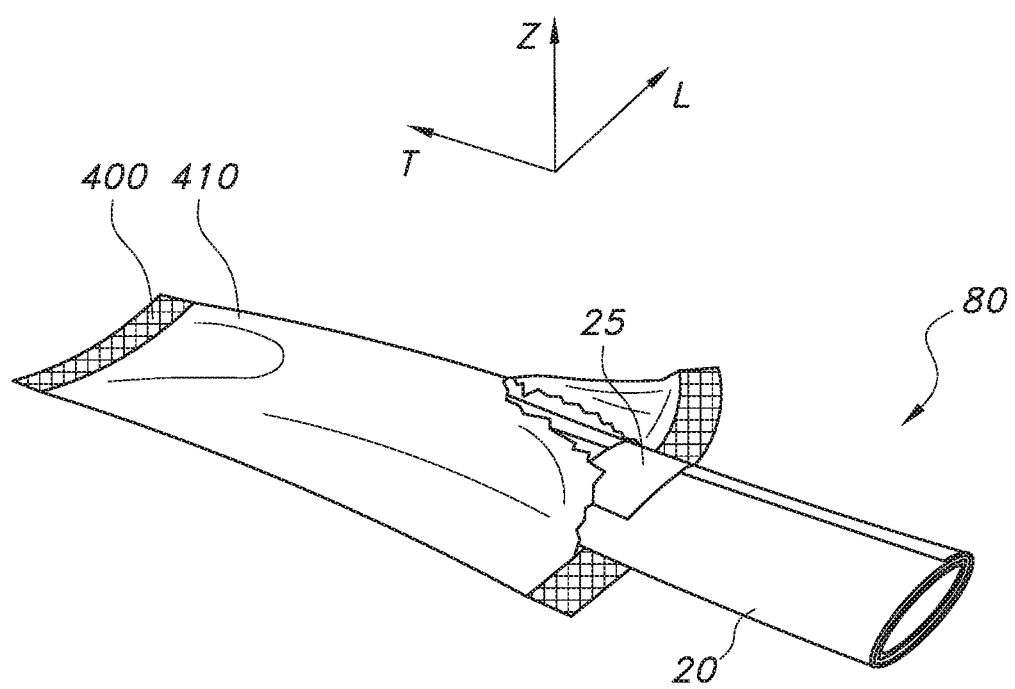
FIG. 11 is a perspective view of a rolled absorbent article, article extension and wrapper of the present invention, with open side edges on the rolled absorbent article, the article being removed from a secondary outer storage pouch layer, but still present in rolled format.

As shown in FIG. 1, the wrapper sheet component 20 may optionally include a tab tape 25 as a fastening means, for maintaining the rolled absorbent article component 40, absorbent article extension component 30 and wrapper sheet component 20 in a rolled configuration (embodiments seen rolled in FIGS. 4, 11, and 12). As illustrated in FIG. 3, such tab tape 25 includes adhesive 25A means to hold the tab tape 25 to the wrapper sheet component outwardly facing surface 21. In an alternative embodiment, the tab tape may be attached to the wrapper sheet component inwardly facing surface 22. The tab tape 25 also includes a strip of adhesive 26 facing the absorbent article component, for securing the wrapper sheet component, absorbent article component, and absorbent article extension component in a rolled configuration, once they have been rolled together for storage. Such a tab tape 25 may be constructed of numerous materials, such as for example a film, nonwoven, combinations of films or nonwovens, or laminate of film and nonwoven materials. While shown with a tab tape 25, the wrapper sheet component 20 need not include such a tab tape, but instead may be fastened in a rolled format by the use of alternative fastening means arrangements, such as lines of pressure sensitive adhesive 27 on the article facing surface 22 of the wrapper sheet component 20 (as seen in FIGS. 1 and 3), more permanent bonding techniques, such as ultrasonic bonding areas, or wrapper encircling ribbons, strings or other such devices that secure the absorbent article component, absorbent article extension component and wrapper sheet component in a rolled configuration (latter not shown).

A top plan view of an alternative embodiment of the panty liner of FIG. 1 is shown in FIG. 2B. In such figure, the absorbent article extension component 30A is shown as being separated by a relatively larger spatial gap along the longitudinal direction from the absorbent article (panty liner) component 40. The absorbent article extension component 30A is in the shape of an oval. A top plan view of yet another alternative embodiment of the panty liner of FIG. 1 is shown in FIG. 2C, in which the absorbent article extension component 30B is shown as a partially rounded geometric shape, separated along the longitudinal direction from the absorbent article component. In FIG. 2D, the generally same shaped absorbent article extension component 30C (but larger than 30B) is shown in a closely bordering spatial configuration with the absorbent article component. The peripheral edges are adjacent and almost touching. As shown in FIG. 2E, the absorbent article extension component 30 includes an overlapping portion 35 that overlaps the absorbent article component 40. An exploded cross-sectional view of the panty liner of FIG. 2E is shown in FIG. 3B, taken along line 3B-3B. In yet another alternative embodiment, as shown in FIG. 2F, the absorbent article extension component 30D is shown in top plan view, adjacent the absorbent article component 40 along a longitudinal side edge 41 of the absorbent article component 40, as opposed to being adjacent along an end edge (as seen in previous figures). The separating seam 39 is situated along the absorbent article longitudinal edge. The adhesive strips 68 are shown running along the article and extension longitudinal direction, across the transverse direction. The tab tape 25 is also situated along a longitudinal side edge of the wrapper sheet component 20. In still a further alternative embodiment of the panty liner, as shown in exploded cross-sectional view of FIG. 3A, an absorbent article extension component 30 is shown adhered on an opposing side surface of the wrapper sheet component 20 rather than on the same side surface as the absorbent article component 40.

As seen in the cross-sectional view of the absorbent article component/absorbent article extension component/ wrapper sheet component combination of FIG. 4 (and FIG. 11), in the rolled personal care absorbent article, the wrapper sheet component encloses both the absorbent article component 40 and the absorbent article extension component 30. The rolled configuration has a rolled article outer diameter L8. Desirably in one embodiment, such diameter is between about 0.5 and 5 cm, alternatively, between about 1 and 2 cm, still further alternatively, about 1.5 cm.

Another alternative embodiment of the absorbent article component, absorbent article extension component, and wrapper sheet component combination 10 of FIG. 1 is seen in FIG. 6. As seen in FIG. 6, an absorbent article, absorbent article extension, and wrapper combination 80 includes a differently shaped absorbent article component 81 on a wrapper sheet component 20 than previous figures. The absorbent article component 81 has longitudinal side edges 45 with scallop features 82 along the side edges. A non-scalloped absorbent article extension component 84 lies adjacent an end of the absorbent article component 81, but includes a gap 86 adjacent the absorbent article component 81 along each of the longitudinal side edges, providing a clear visual and tactile indication of the area of eventual separation between the two components. Such edge distinction also provides additional ease for peeling/grasping one of the components away from the other. It should be recognized that while shown with scalloped and straight edges, a wide variety of different peripheral edge shapes are contemplated. As with previous embodiments, a separation seam 39 provides a line for separating each of the adjacent absorbent article and absorbent article extension components from one another.

Figure 7:
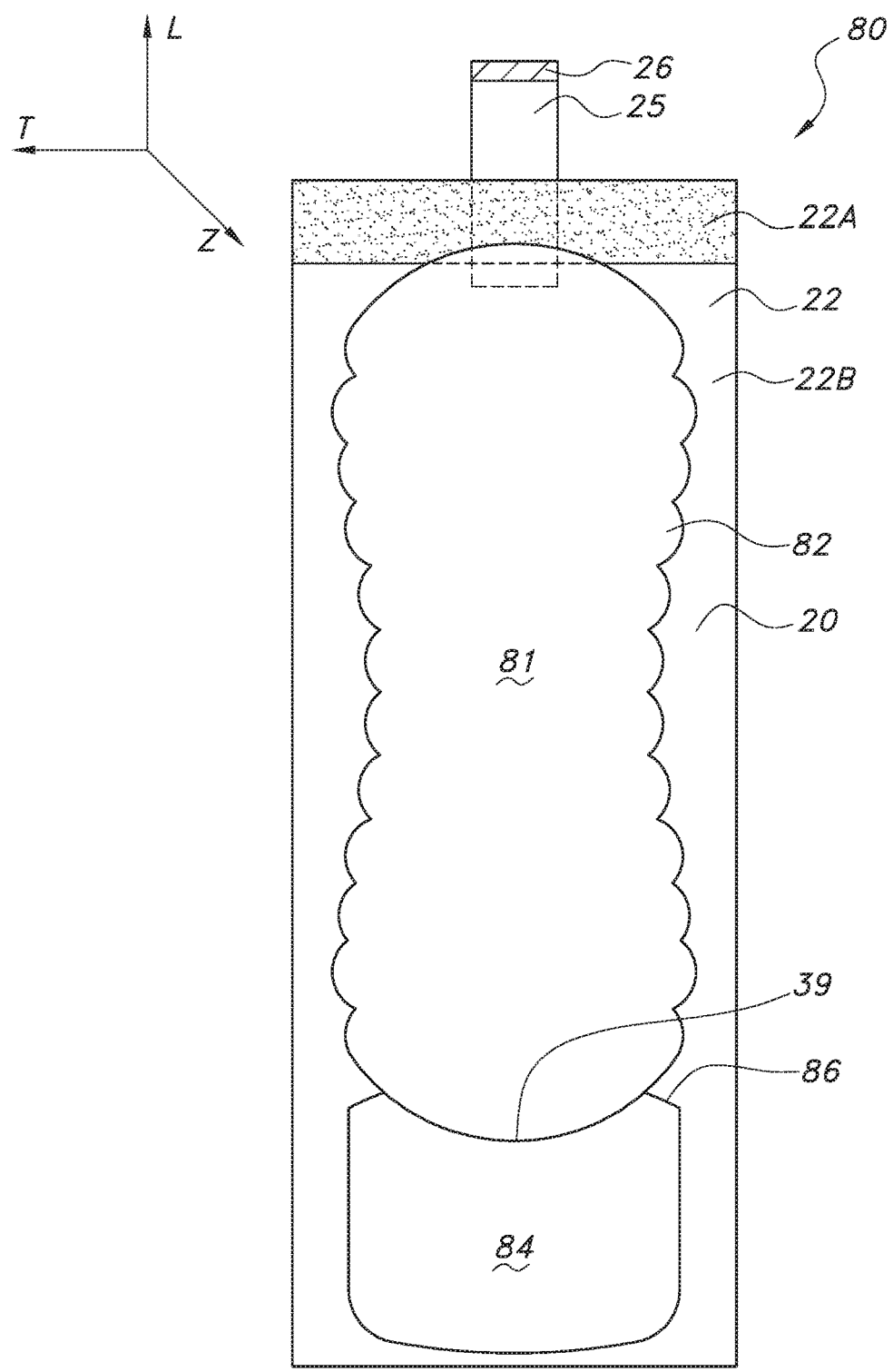
FIG. 7 illustrates a top plan view of still a further alternative embodiment of the unrolled panty liner, liner extension, and associated wrapper of FIG. 1, with select wrapper surface treatment.
Figure 8:
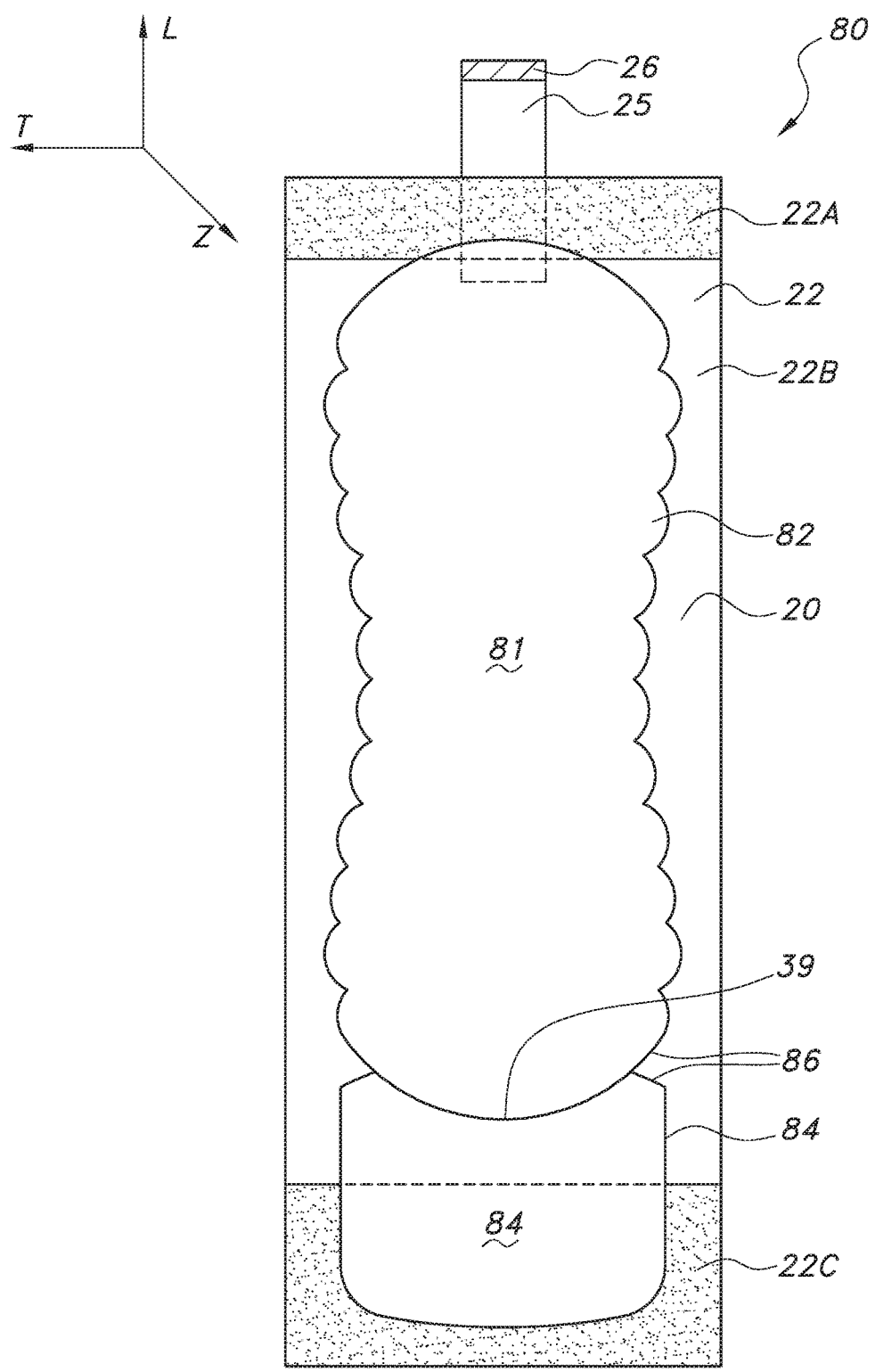
FIG. 8 illustrates a top plan view of yet a further alternative embodiment of the unrolled panty liner, liner extension, and associated wrapper of FIG. 1, with select wrapper surface treatment.

A further alternative embodiment of the absorbent article component, absorbent article extension component, and wrapper sheet component combination of FIG. 1 is seen in FIG. 7. As seen in this figure, the wrapper sheet component 20 has select surface release treatments to facilitate removal of the absorbent article component. For instance, the wrapper sheet component 20, article facing surface 22 has a release treatment (such as silicone) in a middle region (22B) only, and not at least one end region 22A. Alternatively, in a further embodiment as seen in FIG. 8, the wrapper sheet component 22, has two end regions 22A, 22C on the article facing surface 22, that have not been treated to facilitate release of the two components. In such an embodiment, the absorbent article extension component 84 is therefore more likely to stay with the wrapper sheet component upon separation of the absorbent article component 81. Examples of release coatings that may be used is select regions (such as 22B) may be found in U.S. Pat. No. 2,880,862 to Sermattei, U.S. Pat. No. 4,741,948 to Konishi et al., U.S. Pat. No. 4,925,728 to Crass et al., U.S. Pat. No. 5,728,469 to Mann et al., and U.S. Pat. Publications 2004/126576 to Kinning et al., and 2011/202029 to Toro et al., each of which are hereby incorporated by reference thereto in their entirety. Desirably, in one embodiment, the end regions of the wrapper sheet component that are not treated to facilitate release of the components, make up between about 15 percent and 35 percent of the wrapper sheet component, article-facing surface area 22. For the embodiment shown in FIG. 2F in which adhesive strips run along the longitudinal direction, untreated article-facing surface area is in one embodiment, between about 30 and 70 percent.

Figure 9:
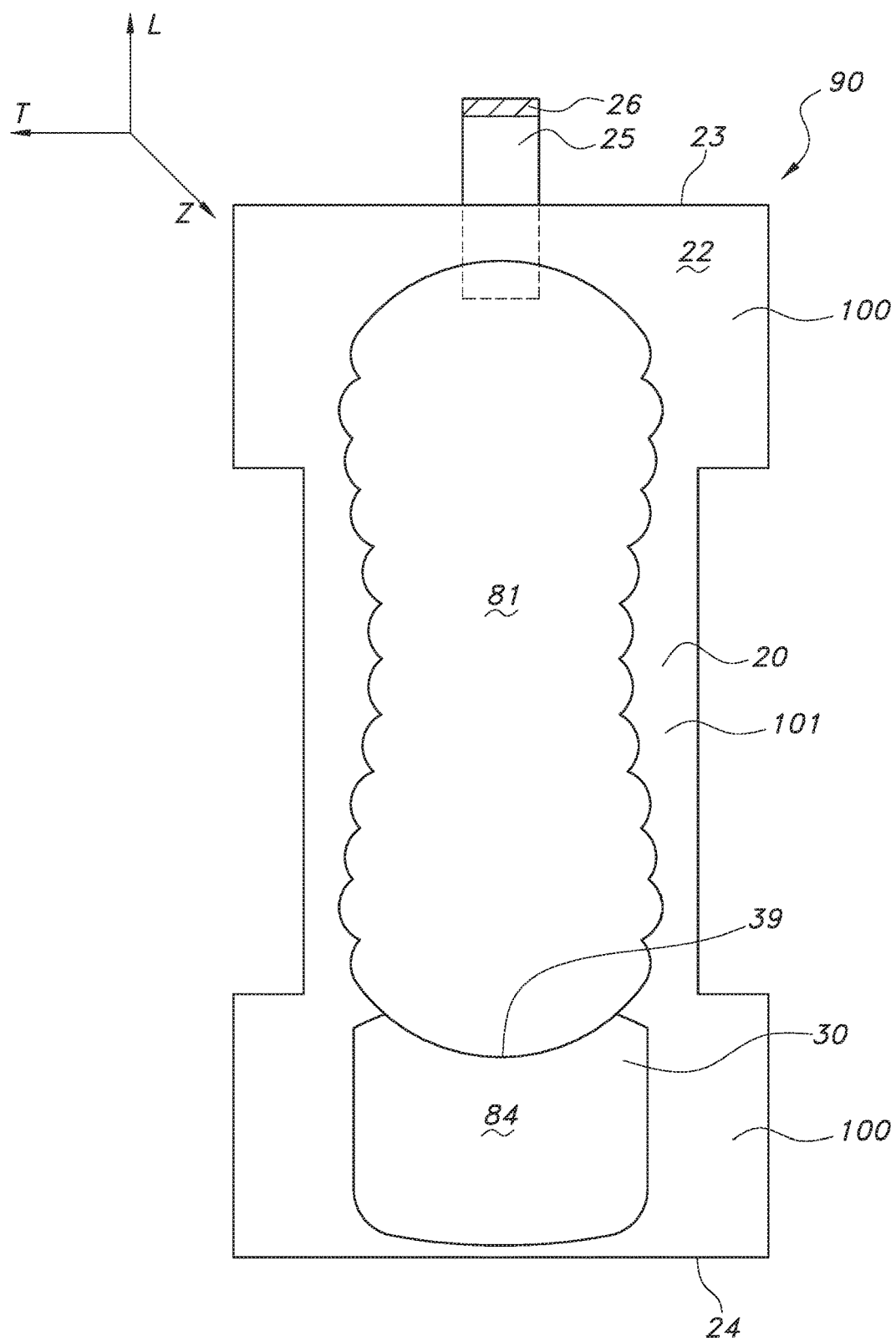
FIG. 9 illustrates a top plan view of still a further alternative embodiment of the unrolled panty liner, liner extension, and associated wrapper of FIG. 1, with alternative wrapper shape.
Figure 12A:
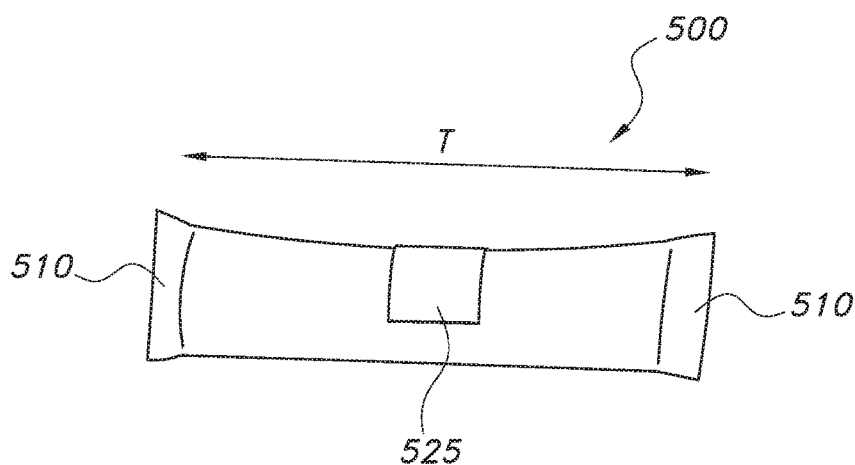
FIG. 12A is a perspective view of an alternative rolled personal care absorbent article of the present invention, without a secondary outer pouch layer, but with sealed side edges.

In still a further alternative embodiment of the combination of FIG. 1, an absorbent article component, absorbent article extension component, and wrapper sheet component combination 90 has a wrapper sheet component 20 including at least two different widths in the transverse direction, along the wrapper longitudinal direction. As seen in FIG. 9, the wrapper sheet component 20 is configured into the shape of an uppercase English letter I, such that it includes two wider areas 100, that are wider along the transverse direction (at the wrapper sheet component ends 23, 24), separated by a narrower wrapper sheet component area 101. In such an embodiment, the absorbent article extension component 30, is desirably situated substantially in one of the two wider areas 100 of the wrapper sheet component 20. Desirably, such wider regions are between about 100 and 150 mm in width (transverse direction), and between about 40 and 100 mm in length (longitudinal direction), while the narrower middle region is between about 30 and 80 mm in width (transverse direction) and between about 100 and 160 mm in length (longitudinal direction). Such wider end regions may be useful in sealing the wrapper sheet component 20 to itself along the longitudinal side edges, without the use of any other outer packaging material, as seen further in FIGS. 12A and 12B. Rather than the combination having open, longitudinally directed side edges (as seen in FIG. 11), the combination is shown in FIG. 12A as having sealed longitudinally directed side edges. The sealing may be accomplished by adhesive, thermal, or ultrasonic bonding for example.

Figure 10:
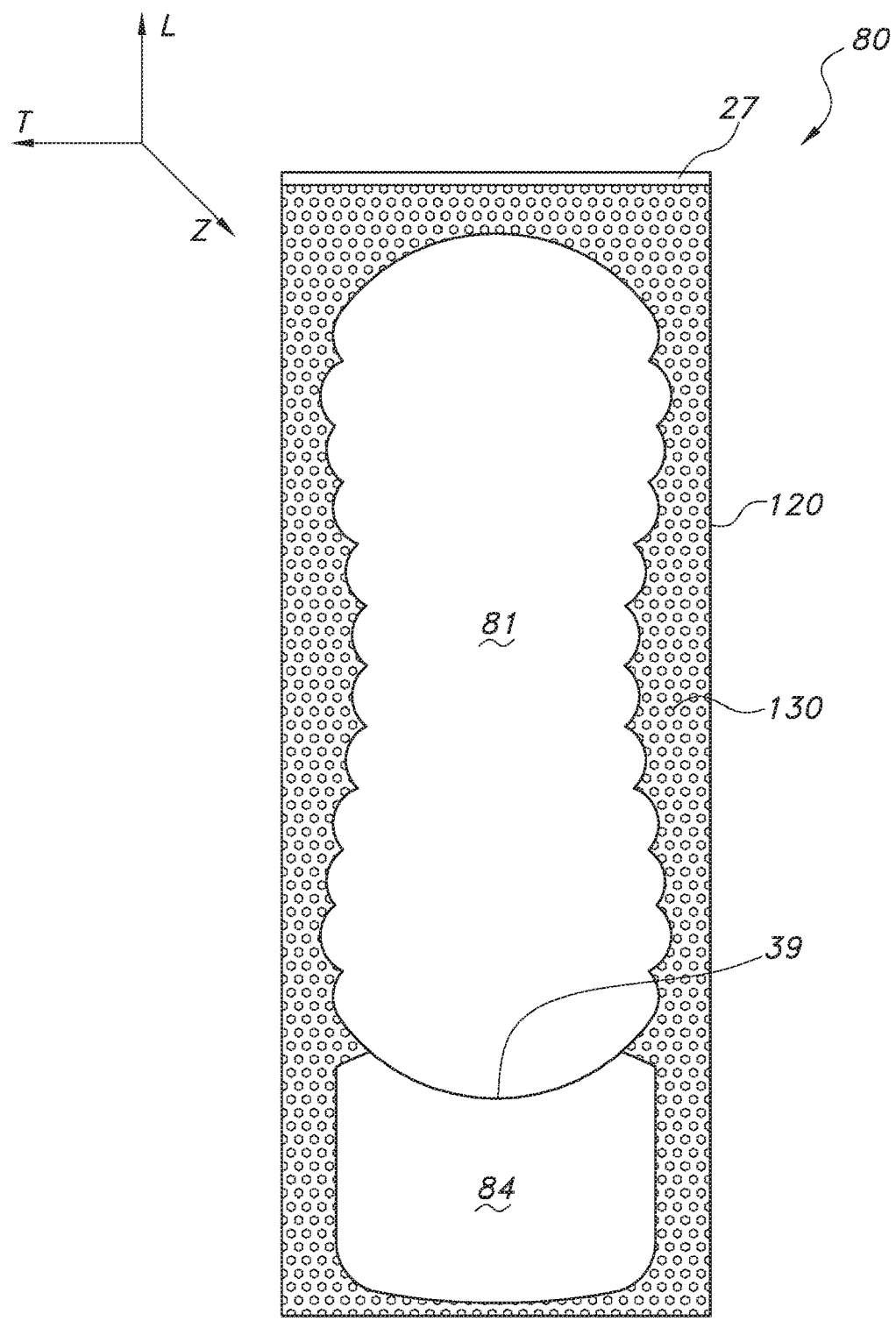
FIG. 10 illustrates a top plan view of still a further alternative embodiment of the unrolled panty liner, liner extension, and associated wrapper of FIG. 1, with alternative wrapper texture.

In yet still another alternative embodiment of the combination of FIG. 1 as seen in FIG. 10, an absorbent article, absorbent article extension, and wrapper combination 90 includes a wrapper sheet component 120 having a textured surface 130 on the article-facing surface in order to facilitate removal of the absorbent article and absorbent article extension components 81, 84 from the wrapper sheet component 120 as desired.

The absorbent article and absorbent article extension components are rolled within the wrapper sheet component following their manufacture as planar layered sheet structures using traditional sheet construction methods. The rolled structure can then be sealed by the noted tab tape, line(s) of adhesive, or other securing devices (such as with encircling string or side sealing means) and can be stored in the wrapper without use of further enclosures or pouches. Such rolled configuration is illustrated in the cross-sectional view of FIG. 4. Such rolled configuration may be open or sealed along its longitudinal side edges. Again, as seen in FIG. 12A, the wrapper sheet component of the absorbent article and wrapper combination 500 is sealed along the longitudinal side edges 510 by a sealing method such as light adhesive, ultrasonic or thermal bonding.

In still a further alternative embodiment, the rolled absorbent article 80 may be stored in a secondary tubular outer pouch if desired. Such outer pouch may be constructed of a wide variety of materials, such as film, nonwoven, combinations of films or nonwovens, or laminates thereof. As can be seen in FIG. 11, such a rolled absorbent article combination 80 may be taped 25 after rolling and stored in an individual outer pouch 410 that is itself sealed at the edges 400, such as by ultrasonic bonding. Such secondary tubular outer pouch 410 is desirably sealed at the ends for discretion, and clean storage of the absorbent article. The rolled absorbent article illustrated in FIG. 11 is actually compressed in its configuration, such that its ends reflect a more oval cross-sectional shape, rather than a circular cross-sectional shape. In a sense, therefore, it is folded along its transverse direction (in addition to being rolled), such that its ends are flattened where the secondary outer pouch is sealed 400. The longitudinal edges of the absorbent article and wrapper combination 80 are still open, rather than being sealed. Upon removal from such a pouch, the tab tape 25 can be separated and the rolled absorbent article unrolled and separated from the wrapper sheet component 20 for use. The rolled absorbent article can therefore be stored in a format that makes identification of the article difficult by non-users, so as to avoid embarrassment by a consumer, and which can easily be stored in a pocket or purse prior to use, or upright in a bag, carton or ornamental container.

The absorbent article component, absorbent article extension component, and wrapper sheet component combination 10 may be made from conventional sheet materials. Additionally, while not shown in the exploded cross-sectional views, conventional construction adhesive may hold the various layers together, in addition to other bonding techniques, such as thermal bonding, ultrasonic bonding, mechanical bonding, hydro-entangling or a combination thereof.

The topsheet layer 42 may be manufactured from any number of conventional materials commonly used as a user-facing surface on an absorbent article. For example, non-limiting examples of such topsheet materials include fibrous nonwoven sheet materials, such as spunbond, spunlace, meltblown, and carded web materials (such as thermally bonded carded webs (TBCW), through-air bonded carded webs (TABCW)), fibrous woven sheet materials, apertured film materials, and laminate combinations of the foregoing materials. Further, monolayered or multilayered sheet materials of the foregoing can also be used as the topsheet layer. Particularly, carded web materials may be made from staple, bicomponent fibers as are known in the art. Materials that may be used in the topsheet layer include synthetic fibers, such as polyolefinic materials, and natural fibers, such as cottonspunlace. Such topsheet layers may be apertured, embossed and/or treated with surfactant so as to manipulate the hydrophobicity/hydrophilicity of the topsheet layer(s) in order to enhance fluid transport properties (since the topsheet layer is the first layer to contact body exudates upon excretion from a user's body). The topsheet layer 42 may also be treated so as to impart other properties to the user-facing surface. Examples of additional treatments include application of skin health agents, coloring agents, odor control agents, stain masking agents and the like.

Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety.

The topsheet layer(s) 42 may also be made from two or more different nonwoven or film materials, with the different materials placed in separate locations laterally across the topsheet layer 42 along the absorbent article component (and/or absorbent article extension component) transverse direction (not shown). For example, the topsheet layer may be a two layer (such as in the same or two different horizontal planes) or multi-component material with a central longitudinally directed section positioned along and straddling the longitudinal centerline of the article or extension, with lateral side-cover sections flanking and joined to each side (or side longitudinal edge) of a central longitudinally directed topsheet layer section. The central topsheet section may be made for example, from the aforementioned TABCW materials or it may be made from a perforated film. The lateral side-cover sections may be made from a different fibrous nonwoven material which is joined to the central longitudinally directed section, such as by adhesive or thermal bonding. Such a two layer (also known as dual cover) configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. Such a two layer topsheet material (dual cover or bicomponent topsheet) can offer the feeling of dryness in the center longitudinally directed section, and a soft feeling along the side-cover longitudinally directed sections. It is also contemplated that such two layer topsheet materials may additionally include longitudinally extending elastic strand components (not shown) along their side edges to lift up components of the side-cover materials during use, thereby forming physical barriers or cupping features on the article so as to allow a fit more closely aligned to the body of a user.

The basis weight of nonwoven webs to be used as topsheet layers may generally vary, such as from about 5 grams per square meter ("gsm") to 150 gsm, in some embodiments from about 10 gsm to about 125 gsm, and in some embodiments, from about 15 gsm to about 120 gsm. Desirably, in one embodiment, the topsheet layer is a through-air bonded carded web having a basis weight of between about 20 gsm and 40 gsm. In another embodiment, such topsheet layer is a 100 percent cotton spunlace material having a basis weight of between about 20 and 50 gsm, desirably about 30 gsm. It is desirable for the size and shape of the topsheet and backsheet layers to be the same, bonded together at their edges.

As noted, in one embodiment, subjacent the topsheet layer 42 in the depth direction Z, is one or more interiorly situated absorbent core layers 43 and optional fluid management layers, designed to transport or retain body exudates that have passed through the topsheet layer 42. As shown in FIG. 3, between the topsheet layer 42 and the backsheet layer 44 (and desirably between the topsheet layer 42 and the absorbent core layer 43), one or more conventional fluid transfer layers 51, fluid surge layers, fluid distribution layers, fluid delay layers or fluid wicking layers may optionally be present. Such additional fluid transfer layers include, but are not limited to, bonded carded webs, hydroentangled nonwoven webs, or spunbond webs desirably containing fibers treated with or containing one or more topical agents that improve the contact angle with the bodily fluid and/or modify the flow properties of the bodily fluid to be transported/retained. A secondary and optional fluid distribution layer 51 is also illustrated between the optional absorbent core layer 43 and the backsheet layer 44 in FIG. 3.

If present in an embodiment, the absorbent core layer 43 includes a user-facing surface 43A and a garment-facing surface 43B. The absorbent core layer 43 functions to absorb and preferably "lock-up" and retain the bodily fluids that pass into the absorbent article component 40 (and optionally into the absorbent article extension component 30) through the topsheet layer 42. The absorbent core layer 43 can itself comprise a single layer or multiple layers and these one or more layers can themselves comprise similar or different materials. Highly absorbent core layers 43 often include, but are not limited to, batts or webs containing wood pulp fibers, superabsorbent particles or fibers (also known as SAP or SAM), synthetic wood pulp fibers, synthetic fibers, coformed materials, and combinations thereof. The absorbent core layer 43 may comprise any one of a number of materials and structures, the particular selection of which will vary with the desired loading capacity, flexibility, body fluid to be absorbed and other factors known to those skilled in the art. By way of example, suitable materials and/or structures for the absorbent core layer 43 include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States patent publication 2010/0174260 to Di Luccio et al., each of which is hereby incorporated by reference thereto in its entirety.

The shape of the absorbent core layer 43 (while generally shown as a dog-bone configuration to mimic the outer peripheral shape of the absorbent article component 40) can vary as desired and can comprise any one of various shapes including, but not limited to, generally triangular, rectangular, dog-bone and elliptical shapes. In one embodiment, the absorbent core layer 43 has a shape that generally corresponds with the overall peripheral shape of the absorbent article component 40 and absorbent article extension component 30 such that the absorbent core layer 43 terminates proximate a peripheral seal region 46 around both components. The dimensions of the absorbent core layer 43 can be substantially similar to those of the absorbent article component 40 and absorbent article extension component 30, however it will be appreciated that the dimensions of the absorbent core layer 43 while similar, will often be slightly less than those of the overall absorbent article component and absorbent article extension component in order to be adequately contained therein, and desirably sealed around the edges. As noted with respect to the topsheet layer 42, there is a respective absorbent article core layer 43C and absorbent article extension core layer 43D in one embodiment. Desirably in one embodiment, the absorbent core layer is a spunlace web material, having a basis weight of between about 20 and 80 gsm, alternatively between about 30 and 80 gsm, alternatively between about 30 and 50 gsm. Such absorbent core layer may in one embodiment, be constructed of a blend of synthetic fibers in a spunlace web such as for example, a blend of PET and rayon fibers, or alternatively, a homogeneous layer of 100 percent rayon fibers, air-laid materials, or foam rubber materials. As illustrated, the absorbent core layer 43 if present, is positioned between the topsheet layer 42 and backsheet layer 44 and may be present in one or both of the absorbent article component and the absorbent article extension component.

The individual layers comprising the absorbent article component and absorbent article extension component can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. Conventional construction adhesive layers, while not illustrated, are contemplated as desirably bonding the various layers of the absorbent article component 40 together, and absorbent article extension component 30 together. The adhesive strength of the construction adhesive layers is desirably higher than that of the pressure sensitive garment adhesive layer (strips 38, 48, 68) such that the absorbent article component and absorbent article extension component can each be separately, and easily removed from the wrapper sheet component.

In a further alternative embodiment, the absorbent core layer 43 can be sealed between the topsheet layer 42 and backsheet layer 44 along the perimeter of the absorbent core layer 43 along a peripheral seal region 46 formed by the application of heat and pressure to melt thermoplastic polymers located in the topsheet layer 42 and/or backsheet layer 44. Desirably, in one embodiment, the liquid permeable, user-facing topsheet layer 42 is bonded at least at its periphery, to the garment-facing, backsheet layer 44 at least in the peripheral seal region 46, but may also be bonded to it at other locations inward of the peripheral seal region 46.

The backsheet layer 44 (which includes a respective absorbent article component backsheet 44C and absorbent article extension component backsheet 44D) functions to isolate absorbed fluids from the wearer's garments or bedding, and therefore desirably comprises a liquid-impervious material. In one aspect, the backsheet layer 44 may optionally comprise a material that prevents the passage of liquids but allows air and water-vapor to pass there-through. The backsheet layer 44 can comprise a single layer or multiple layers, and these one or more layers can themselves comprise similar or different materials. Suitable backsheet layer materials include, but are not limited to, polyolefin films, nonwovens, nonwoven laminates, and film/nonwoven laminates. The particular structure and composition of the backsheet layer 44 may be selected from various known films and/or fabrics with the particular material being selected as appropriate to provide the desired level of liquid barrier, strength, abrasion resistance, tactile properties, aesthetics (such as texture and printability) and so forth. Suitable backsheet layer materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety. The backsheet layer may be breathable or nonbreathable, as may be desired. In one embodiment, the backsheet layer is a breathable polyolefinic film having a basis weight of between about 18 and 40 gsm, alternatively between about 20 and 30 gsm, such as of a polyethylene film.

The wrapper sheet component 20 itself, may be formed from conventional absorbent article wrapper materials, such as polymeric films and/or fibrous nonwoven sheet materials, or laminates thereof, either of monolayer or multilayer materials. In one embodiment, the wrapper sheet component is a polyethylene film having a basis weight of between about 20 and 30 gsm, such as about 25 gsm. The wrapper sheet component 20 contacts the garment adhesive of the backsheet layer in a contact region 28, in which the absorbent article component has a contact region 28A, and the absorbent article extension component has a contact region 28B. Desirably, in one embodiment where the wrapper sheet component 20 is to contact the garment adhesive strips 48, 38 (blocks, strips, or continuous adhesive layer as the case may be), the wrapper sheet component is coated with a release coating along the entire surface or only a portion of the contact region 28 such that its ability to be peeled away from the pressure sensitive garment adhesive is enhanced (made easier). In an alternative embodiment, the contact region is only coated immediately adjacent the absorbent article component garment adhesive (strips 48). The release coating to be applied to the contact region 28 on the article-facing surface 22 of the wrapper sheet component 20 can be of conventional formulations, such as for example silicone or other coatings.

If included in an embodiment, an outer tubular pouch enclosure can be constructed of traditional film and/or nonwoven materials, such as for example, a polyolefinic film having a basis weight of between about 20 and 40 gsm, alternatively a polyethylene film of about 25 gsm. If included in an embodiment, a strip of pressure sensitive sealing adhesive may be included on a wrapper sheet component 27, of a basis weight of between 10 and 50 gsm, alternatively between about 15 and 25 gsm having a line width of between about 1 and 15 mm, alternatively between about 3 and 8 mm.

The rolled personal care absorbent article (including the three components) can be manufactured in a number of ways, following manufacture of the individual components. In one embodiment, the absorbent article component and one or more absorbent article extension components may be manufactured as a unitary structure and separated completely or with a perforation seam prior to being placed on a wrapper sheet component. Alternatively, the unitary structure can be placed on the wrapper sheet component and then one or more perforation or separation seams (multiple seams if there are more than one absorbent article extension components) can be created between those structures which are to become the absorbent article and absorbent article extension components. The combination can then be rolled and secured in a roll configuration, such as with the tab tape, pressure sensitive adhesive strip, or roll encircling device as previously discussed.

Figure 12B:
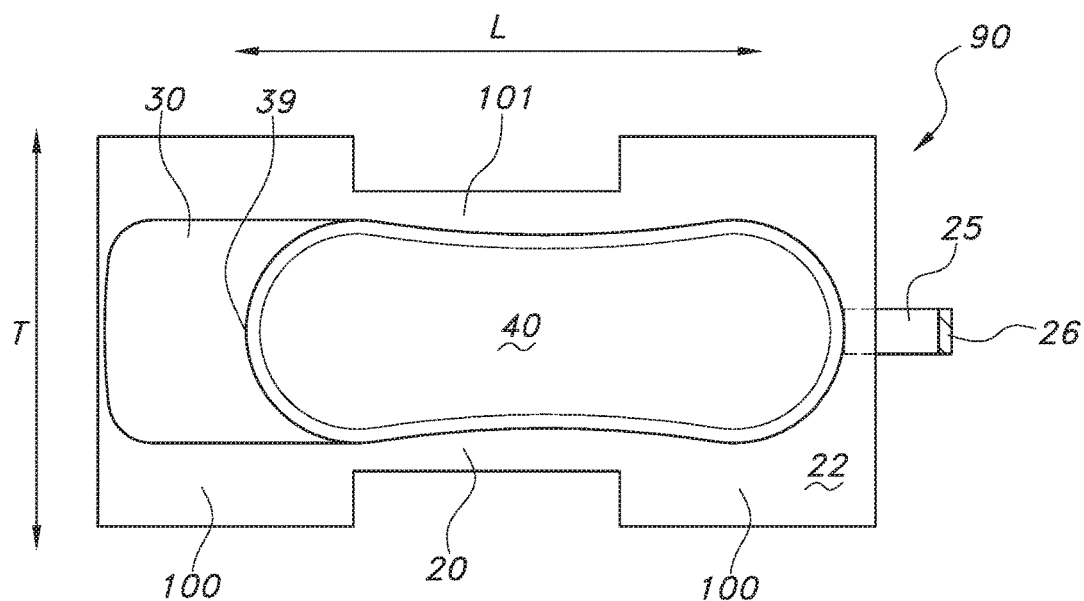
FIG. 12B is a top plan view of the alternative rolled personal care absorbent article of FIG. 12A in unrolled flat format.

In another embodiment, while the materials of the rolled personal care absorbent article are each produced along a machine direction, the components can be attached to a continuous wrapper sheet component, and the three components (the absorbent article component, absorbent article extension component, and wrapper sheet component) can be moved on an article production/rolling machine along the article transverse direction, for final assembly and rolling. For example, in a first embodiment, following the placement of a series of the absorbent article components and absorbent article extension components sequentially on a continuously running wrapper sheet component, the separate tab tapes can be added to the series of combinations 10, and individual combinations can then be cut from the continuously running sheet. The individual combinations can then be individually rolled and sealed, and if desired, each inserted into a further secondary enclosure such as a pouch. Alternatively, for embodiments as shown in FIGS. 9 and 12B, such individual combinations can be sealed as a unit without the use of a secondary outer packaging. As previously described, select portions of the wrapper sheet component 20 in FIGS. 9 and 12B have extended widths along the transverse direction 100, compared to other portions 101. In the figures illustrated, the end portions of the wrapper sheet component 100 have extended widths compared to middle or intermediate portions/regions, although it is contemplated that in alternative embodiments, the intermediate regions may have extended widths rather than the end portions. In either event, the portions with extended widths would be sealed along their longitudinally directed outer-most edges (lateral-most edges at least in the extended width portions) after the combination 90 has been rolled. Such sealing may be accomplished by several bonding techniques, such as for example, adhesive, ultrasonic, thermal bonding or a combination thereof.

It is contemplated in one embodiment, that a series of absorbent article components and absorbent article extension components may be applied to a continuous wrapper sheet component, with the absorbent article components and absorbent article extension components applied as unitary structures that are then separated on the continuous wrapper sheet component using seam-forming technology. It is further contemplated that such components may be constructed as a unitary structure that is then separated by seam-forming technology and then separately applied to the continuous wrapper sheet component. Finally, it is also contemplated that such components may be separately constructed and applied to the continuous wrapper sheet component with select spatial distances between them.

Following the manufacture, rolling, and sealing of the rolled personal care absorbent article, the rolled personal care absorbent article may be stored in its individual wrapper sheet component only, alternatively, in its individual wrapper sheet component and in a secondary packaging enclosure, such as a sealed pouch, or in a further box, carton or other packaging enclosure, or a combination thereof, prior to use by a consumer. The individual rolled personal care absorbent article may be carried in a purse or pocket inconspicuously, until use is desired.

Once the rolled article is removed from any secondary enclosure, unsealed, and unrolled (such as by removal of the tab tape, adhesive strip, or wrapping string/ribbon and unrolling along the appropriate direction), the absorbent article component 40 is the initial component 60 (as seen in FIG. 1) that is desirably removed by a consumer, desirably once the wrapper sheet component 20 has been unrolled to a relatively flat configuration. Such absorbent article component 40 would be removed from the wrapper sheet component 20 by being either peeled off the wrapper sheet component from an end edge, 49, 50; alternatively, with the use of an assisting tab (not shown) which could extend from an article end edge; or alternatively, by folding the combination 10 at the separating seam 39, and forcing the article end 49 adjacent the seam to move up and away from the absorbent article extension component 30 edge via slight upward pressure being exerted from beneath the wrapper sheet component 20 (at the outwardly facing surface 21). The absorbent article component 40 can then be peeled away from the absorbent article extension component 30 and applied to a user's undergarment.

As noted, once the absorbent article component 40, in this case a panty liner, is separated from the wrapper sheet component 20, it may be used by a consumer. The absorbent article extension component 30 initially remains with the wrapper sheet component 20 as seen in FIG. 2. The absorbent article extension component 30 may later be separated from the wrapper sheet component 20 (as seen in FIG. 2A) by a consumer, and used to extend the panty liner length or width within an undergarment. Such absorbent article extension component 30 may be placed adjacent the previously positioned panty liner (such as adjacent an end or longitudinal side edge) to create an extended panty liner as needed. Alternatively, since the absorbent article extension component 30 is in one embodiment, desirably made from the same layer types and materials as the absorbent article component, it also includes a soft and/or flexible user-facing topsheet layer. It may also include an absorbent core layer. With such layers, the absorbent article extension component may be used, while attached, or unattached to the wrapper sheet component 20, as a wipe-like device and discarded as a unit or separately after soiling.

FIG. 2 illustrates the absorbent article component 40 once it has been separated from the associated wrapper component 20. In such a situation, the absorbent article extension component 30 remains with the wrapper component 20 for discarding or later use as a wipe-like device or article extension. The absorbent article extension component 30 can be removed from the wrapper sheet component 20 if desired, in a later step. Such extension can be placed either immediately adjacent the absorbent article component 40 edge (49,50, 41) that has previously been put in an undergarment, or over an end edge 49,50.

In the case of the embodiment of FIG. 2E, prior to removal of the absorbent article component 40, the free edge 36 of the overlapping absorbent article extension component 30 would first need to be lifted away from the absorbent article component, before the absorbent article component is removed from the associated wrapper sheet component 20. Alternatively, if desired by a consumer, the absorbent article extension component 30 of FIG. 2E can first be removed and placed in a user's undergarment prior to the removal and placement of the absorbent article component 40.

The absorbent article extension component 30 therefore serves the dual purpose of (a) providing initial support on the wrapper sheet component 20 for easy removal of the absorbent article component 40 after the absorbent article/absorbent article extension/wrapper combination 10 has been unrolled, and (b) providing an absorbent article extension 30 or wipe-like device if the consumer determines that an extended pad or liner is desired, based on undergarment size or expected exudate flow for a particular day. The absorbent article extension component 30 allows for the more efficient manufacture of an absorbent article component, since such can be made of the same materials, during the same process of absorbent article component formation, and provides a more rigid support for such on the wrapper sheet component 20 during absorbent article component removal. Such structure also allows for less curling of the unrolled absorbent article component 40 following its removal from the wrapper sheet component, and less curling of the remaining wrapper sheet component 20. The combination of the absorbent article and absorbent article extension components also offers the consumer both components in a proximate location for ease of use.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent personal care article including a longitudinal direction, a transverse direction and a depth direction, said article comprising:
   an absorbent article component, an absorbent article extension component, and a wrapper sheet component each having a longitudinal, transverse, and depth direction, wherein each of said absorbent article component and said absorbent article extension component includes at least a topsheet layer and a backsheet layer, wherein said backsheet layer includes a garment-facing surface on which is situated a garment fastener wherein said garment fastener on said absorbent article component and said absorbent article extension component differs in strength between said absorbent article component and said absorbent article extension component, such that said absorbent article extension component has a greater propensity to stay with said wrapper sheet component than said absorbent article component does with said wrapper sheet component;
   wherein said absorbent article component and said absorbent article extension component each include a peripheral edge, said absorbent article component and said absorbent article extension component each being attached to said wrapper sheet component with said garment fastener, such that said peripheral edges are adjacent one another.

2. The absorbent personal care article of claim 1, wherein said absorbent article and said absorbent article extension components are in a rolled configuration within said wrapper sheet component and secured in said rolled configuration.

3. The absorbent personal care article of claim 2, wherein said adjacent peripheral edges are aligned.

4. The absorbent personal care article of claim 2, wherein said garment fastener is garment adhesive.

5. The absorbent personal care article of claim 2, wherein at least one of said absorbent article component and said absorbent article extension component include an absorbent core layer.

6. The absorbent personal care article of claim 2, wherein said absorbent article component and said absorbent article extension component are manufactured of the same types of layers.

7. The absorbent personal care article of claim 2, wherein said absorbent article component and said absorbent article extension component are manufactured of the same types of materials.

8. The absorbent personal care article of claim 2, wherein said peripheral edges are 30 mm or less from one another.

9. The absorbent personal care article of claim 2, wherein a peripheral edge of said absorbent article extension component overlaps a peripheral edge of said absorbent article component.

10. The absorbent personal care article of claim 2, wherein said absorbent article component and said absorbent article extension component are aligned along either a longitudinal or transverse direction.

11. The absorbent personal care article of claim 2, wherein said rolled configuration is secured by means of a tab tape, adhesive, ribbon, string, or combination thereof.

12. The absorbent personal care article of claim 2, wherein said absorbent article component and absorbent article extension component are visually distinguishable by peripheral edge shape differences, coloration differences, embossment differences, or a combination thereof.

13. The absorbent personal care article of claim 4, wherein said wrapper sheet component includes an article-facing surface, and said wrapper sheet component further includes a release coating selectively positioned on said wrapper sheet component, article-facing surface.

14. The absorbent personal care article of claim 2, wherein said wrapper sheet component includes different widths along said longitudinal direction.

15. The absorbent personal care article of claim 14, wherein said wrapper sheet component has a first end, a second end, and a middle region along said longitudinal direction, and further wherein said first and second ends are wider along said transverse direction than said middle region.

16. The absorbent personal care article of claim 15, wherein said wider first and second ends are sealed along the longitudinal direction.

17. The absorbent personal care article of claim 2, wherein said absorbent personal care article is selected from the group consisting of a panty liner, sanitary napkin, adult incontinence pad, garment insert and bed liner.

* * * * *